(12) United States Patent
Kose et al.

(10) Patent No.: US 10,849,699 B2
(45) Date of Patent: Dec. 1, 2020

(54) CONTROL APPARATUS FOR A CONTINUUM ROBOT SYSTEM

(71) Applicant: CANON KABUSHIKI KAISHA, Tokyo (JP)

(72) Inventors: Hidekazu Kose, Tokyo (JP); Kiyoshi Takagi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 294 days.

(21) Appl. No.: 15/951,037

(22) Filed: Apr. 11, 2018

(65) Prior Publication Data

US 2018/0296282 A1  Oct. 18, 2018

(30) Foreign Application Priority Data

Apr. 18, 2017  (JP) ................. 2017-082323

(51) Int. Cl.
| | |
|---|---|
| *A61B 1/005* | (2006.01) |
| *A61B 34/30* | (2016.01) |
| *A61B 1/008* | (2006.01) |
| *A61B 34/37* | (2016.01) |
| *A61B 34/00* | (2016.01) |

(Continued)

(52) U.S. Cl.
CPC .......... *A61B 34/30* (2016.02); *A61B 1/00006* (2013.01); *A61B 1/008* (2013.01); *A61B 1/0016* (2013.01); *A61B 1/0053* (2013.01); *A61B 34/37* (2016.02); *A61B 34/71* (2016.02); *A61B 1/0058* (2013.01); *A61B 34/74* (2016.02); *A61B 2034/301* (2016.02); *B25J 9/1635* (2013.01); *B25J 9/1651* (2013.01); *G05B 2219/40234* (2013.01)

(58) Field of Classification Search
CPC ......... A61B 34/30; A61B 34/74; A61B 1/008; A61B 1/0058; A61B 1/0053; A61B 2090/508; A61B 2034/301; B25J 9/1635; B25J 9/0015
USPC ...... 700/245, 258; 901/1, 2, 15; 318/568.12; 606/130
See application file for complete search history.

(56) References Cited

U.S. PATENT DOCUMENTS

| | | |
|---|---|---|
| 2005/0209509 A1 | 9/2005 | Belson |
| 2015/0148956 A1* | 5/2015 | Negishi .................. B25J 9/163 700/253 |
| 2017/0066131 A1* | 3/2017 | Kamikawa ............. A61B 34/30 |

(Continued)

*Primary Examiner* — Dalena Tran
(74) *Attorney, Agent, or Firm* — Venable LLP

(57) ABSTRACT

Provided is a control apparatus for a continuum robot system includes: a continuum robot (1), which includes a plurality of curvable portions (111, 112) provided in series in a longitudinal axial direction thereof and each being curvable, and is capable of being moved in the longitudinal axial direction; a drive unit (2) configured to move the continuum robot (1) in the longitudinal axial direction; and a plurality of angle control motors (211, 212) configured to change a distal-end angle ($\theta_1$, $\theta_2$) for each of the plurality of curvable portions (111, 112). The control apparatus includes a drive unit speed calculation/control unit (44) configured to calculate a followable speed, and to control the drive unit (2). The drive unit speed calculation/control unit (44) controls the drive unit (2) to move the continuum robot at a speed equal to or lower than the followable speed.

10 Claims, 11 Drawing Sheets

(51) Int. Cl.
   *A61B 1/00* (2006.01)
   *B25J 9/16* (2006.01)

(56) References Cited

U.S. PATENT DOCUMENTS

2018/0099422 A1\* 4/2018 Yoon ...................... B25J 13/084
2018/0194009 A1\* 7/2018 Kojima ................. B25J 9/1692

\* cited by examiner

CONTROL APPARATUS FOR A CONTINUUM ROBOT SYSTEM

BACKGROUND

Technical Field

This disclosure relates to a control apparatus for a continuum robot system.

Description of the Related Art

In U.S. Patent Application Publication No. 2005/0209509, there is disclosed an endoscope including a controller configured to control the posture of a curvable portion of a continuum robot, in which the controller is configured to control a following curvable portion so as to follow a path through which a curvable portion located at the head of the continuum robot in the traveling direction. In the following description, such posture control is referred to as "follow-the-leader control". According to the endoscope including the controller configured to perform the follow-the-leader control, when the endoscope is inserted into a body cavity of a subject to be examined being an insertion target of the endoscope, a user is only required to operate the posture of the curvable portion located at the head in an insertion direction in order to automatically control the following curvable portion so as to avoid contacting a body tissue of the subject to be examined. At the time of extraction, the posture of each curvable portion is automatically controlled so that the curvable portion follows the path through which the endoscope passed at the time of insertion, and hence the user is not required to manipulate the posture of the curvable portion. In this manner, through use of the follow-the-leader control, it is possible to reduce a burden imposed on the user when the continuum robot is inserted or extracted.

SUMMARY

According to one embodiment of this disclosure, there is provided a control apparatus for a continuum robot system, the continuum robot system including: a continuum robot, which includes a plurality of curvable portions provided in series in a longitudinal axial direction of the plurality of curvable portions and each being curvable, and is capable of being moved in the longitudinal axial direction; a movement driving unit configured to move the continuum robot in the longitudinal axial direction; and a posture changing unit configured to cause each of the plurality of curvable portions to curve, to thereby change a posture of the each of the plurality of curvable portions, the control apparatus including: a movable drive control unit configured to control the movement driving unit; and a speed calculation unit configured to calculate a maximum value of a moving speed of the continuum robot in the longitudinal axial direction, which enables the posture changing unit to cause the posture of each of the plurality of curvable portions to agree with a target posture before the movement driving unit completes moving the continuum robot in the longitudinal axial direction by a predetermined distance, wherein the movable drive control unit is configured to set the moving speed of the continuum robot in the longitudinal axial direction, which is being moved by the movement driving unit, to have a value equal to or smaller than the maximum value.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

In follow-the-leader control, the posture of a curvable portion of a continuum robot is changed so that the curvable portion follows a target path, and hence it is required to change the posture of the curvable portion at a high speed in order to perform an insertion/extraction operation at a high speed. However, in general, there exist upper limits to the response speeds and driving speeds of actuators and drive transmission mechanisms that are configured to change the posture of the continuum robot. This requires a certain amount of time after a drive command is issued to an actuator (after the actuator starts its operation) until the posture of the curvable portion agrees with a target posture. Therefore, when the continuum robot is inserted or extracted at a high speed, the change in posture of the curvable portion may fail to follow the shape of the target path, and the actuator may deviate from the target path.

An object to be achieved by this disclosure is to prevent the continuum robot from deviating from the target path when the continuum robot is advanced or reversed.

Now, embodiments of this disclosure are each described below in detail with reference to the accompanying drawings. The embodiments of this disclosure are each described by taking an example of applying a continuum robot system to a flexible endoscope. In recent years, minimally invasive medical treatment for reducing a burden on a patient and improving quality of life (QOL) after treatment or examination has been attracting attention. Examples of the minimally invasive medical treatment include surgery or examination using an endoscope. For example, laparoscopic surgery enables a surgical wound to be made smaller than in the case of laparotomy surgery, which has hitherto been adopted, and is thus advantageous not only in that the hospitalization period required after surgery can be shortened but also in that the laparoscopic surgery is cosmetically superior. Endoscopes used for minimally invasive medical treatment are roughly classified into rigid-type endoscopes and flexible endoscopes. Of those, the flexible endoscope has an insertion portion formed of a member capable of being curved through an operator's manipulation, and hence it is possible to observe the entirety of a wide range by manipulating the curving angle at the tip of the endoscope.

First Embodiment (Example of Configuration of Continuum Robot System)

Figure 1A:
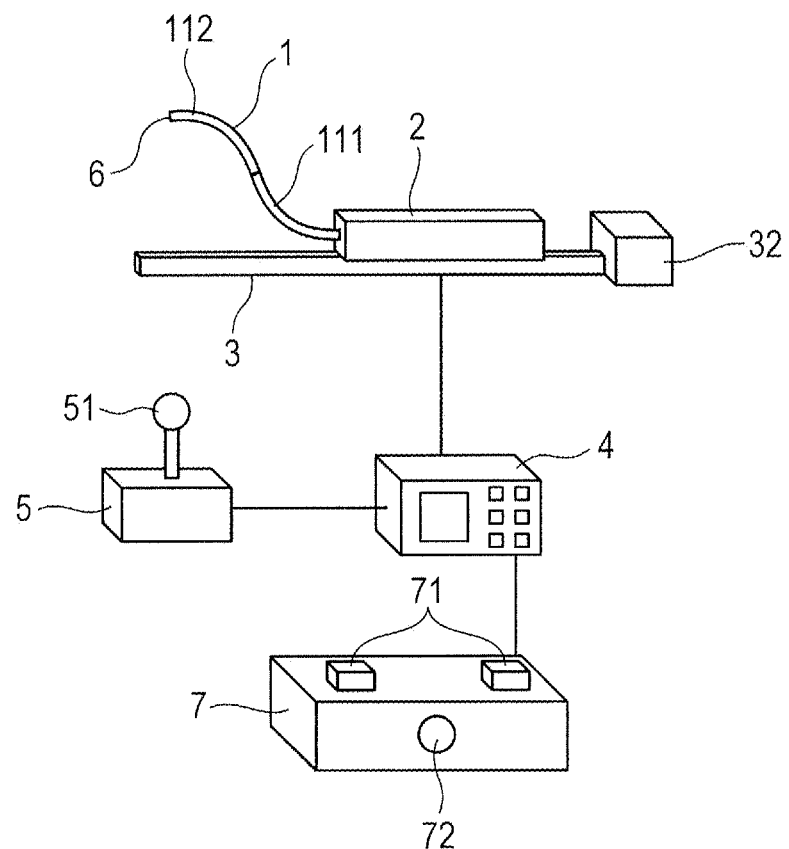
FIG. 1A and FIG. 1B are schematic diagrams for illustrating a configuration example of a continuum robot system in a first embodiment of this disclosure.
Figure 1B:
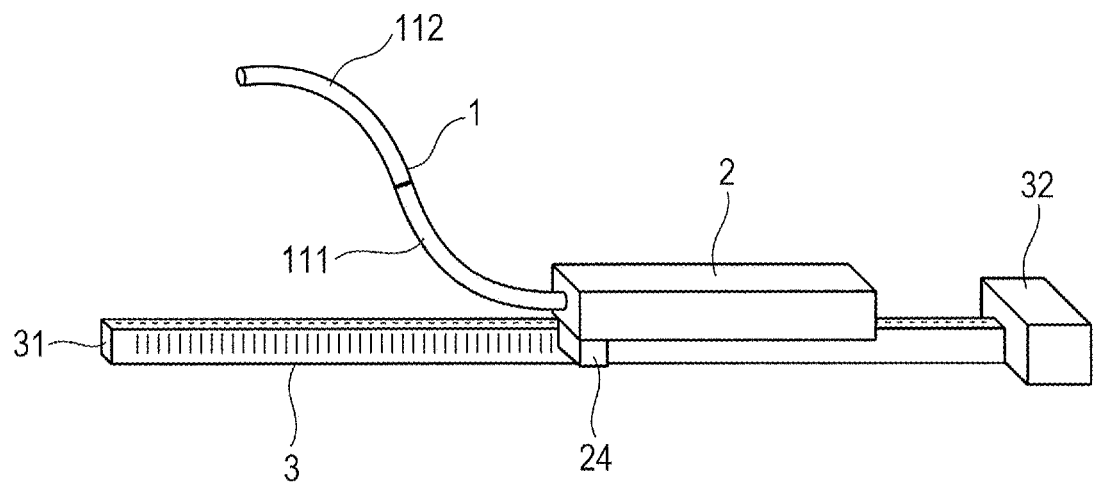

First, a configuration example of a continuum robot system in a first embodiment of this disclosure is described. FIG. 1A and FIG. 1B are schematic diagrams for illustrating the configuration example of the continuum robot system in the first embodiment. In FIG. 1A, an overall configuration of the continuum robot system is illustrated, while in FIG. 1B, a continuum robot 1, a drive unit 2, a linear guide 3, and a movement driving unit 32 are illustrated. As illustrated in FIG. 1A and FIG. 1B, the continuum robot system in the first embodiment includes the continuum robot 1, the drive unit 2, the linear guide 3, the movement driving unit 32, a control apparatus 4, an angle input portion 5, a guide manipulating portion 7, and a camera 6. Note that, the kinds and configurations of devices included in the continuum robot system are not limited to those illustrated in the example of FIG. 1A and FIG. 1B.

The continuum robot 1 includes a plurality of curvable portions provided so as to be connected in series in a longitudinal axial direction of the plurality of curvable portions. Each of the plurality of curvable portions is capable of being curved in an arc shape. Then, each of the curvable portions is driven to be deformed by each of a plurality of posture changing units (actuators) provided to the drive unit 2, to thereby have the posture changed. The configuration example of the continuum robot 1 is described later in detail. In the first embodiment, of the plurality of curvable portions provided so as to be connected in series, a curvable portion located farthest from the drive unit 2 is referred to as "distal-end curvable portion", and a curvable portion located closest to the drive unit 2 on the side opposite to the distal-end curvable portion is referred to as "proximal-end curvable portion". In regard to each individual curvable portion of the continuum robot 1 as well as the entire continuum robot 1, an end portion on the side farther from the drive unit 2 in the longitudinal axial direction is referred to as "distal end", and an end portion on the side opposite to the distal end and closer to the drive unit 2 is referred to as "proximal end". The continuum robot 1 is capable of moving in the longitudinal axial direction, and performs an advancing/reversing action together with the drive unit 2 by a driving force of the movement driving unit 32. In the first embodiment, a movement in the longitudinal axial direction with the distal-end curvable portion being used as the leader is set as an advancing action, and a movement in the longitudinal axial direction with the proximal-end curvable portion being used as the leader is set as a reversing action.

The camera 6 is provided at the distal end of the distal-end curvable portion. No particular limitations are imposed on the configuration of the camera 6, and various known cameras used for a flexible endoscope can be employed.

The drive unit 2 is capable of reciprocating in the longitudinal axial direction of the linear guide 3. The movement driving unit 32 causes the drive unit 2 to perform an advancing/reversing action along the linear guide 3 under the control of the control apparatus 4. When the drive unit 2 performs an advancing/reversing action (linear movement in this example) by the driving force of the movement driving unit 32, the continuum robot 1 performs an advancing/reversing action in the longitudinal axial direction. The linear guide 3 includes a scale 31 for indicating a position in the longitudinal axial direction, and the drive unit 2 includes a sensor 24 configured to detect the scale 31 and a speed/position calculation unit (not shown). The speed/position calculation unit of the drive unit 2 calculates the moving speed of the advancing/reversing action of the drive unit 2 and the current position of the drive unit 2 from the result of detecting the scale 31 by the sensor 24, and outputs (transmits) the moving speed and the current position to the control apparatus 4. No particular limitations are imposed on the configuration of the movement driving unit 32. For example, various known linear actuators can be employed.

The guide manipulating portion 7 is a device to be manipulated by the user (operator) of the continuum robot system. The guide manipulating portion 7 includes an advancing/reversing button 71 being a manipulation member for transmitting a command for an advancing/reversing action to the control apparatus 4, and a volume 72 for inputting (setting) a required moving speed $v_{ref}$ of the advancing/reversing action of the drive unit 2. The "required moving speed" refers to the moving speed of the advancing/reversing action of the continuum robot 1 (drive unit 2), which is requested by the user. The guide manipulating portion 7 outputs the command for the advancing/reversing action of the drive unit 2 to the movement driving unit 32 in accordance with the manipulation of the advancing/reversing button 71, and outputs the required moving speed $v_{ref}$ to the movement driving unit 32 in accordance with the manipulation of the volume 72. No particular limitations are imposed on the specific configuration of the guide manipulating portion 7. Any guide manipulating portion 7 may be used as long as the guide manipulating portion 7 is configured to allow the user to perform a manipulation for instructing the movement driving unit 32 to perform the advancing/reversing action of the drive unit 2, and to allow the user to perform a manipulation for inputting (setting) the required moving speed $v_{ref}$ of the drive unit 2.

The angle input portion 5 is a device configured to allow the user to input (set) the distal-end angle of the distal-end curvable portion of the continuum robot 1. The "distal-end angle of the distal-end curvable portion" refers to an angle formed, in a plane in which the continuum robot 1 is changed in posture (changed in angle), between a "straight line passing along the distal end of the distal-end curvable portion perpendicularly to the center line of the distal-end curvable portion" and a "straight line passing along the proximal end of the proximal-end curvable portion perpendicularly to the moving direction of the advancing/reversing action of the proximal-end curvable portion". The angle input portion 5 includes, for example, a lever 51 being a manipulation member for inputting (setting) the distal-end angle of the distal-end curvable portion. The user can input (set) the distal-end angle of the distal-end curvable portion through the manipulation of the lever 51, and the input distal-end angle of the distal-end curvable portion is output (transmitted) to the control apparatus 4. No particular limitations are imposed on the specific configuration of the angle input portion 5. Any angle input portion 5 may be used as long as the angle input portion 5 is configured to allow the user to input the distal-end angle being the target posture of the distal-end curvable portion, and to allow the user to transmit the input distal-end angle to the control apparatus 4.

The control apparatus 4 drives the drive unit 2 based on the command for an advancing/reversing action and the required moving speed $v_{ref}$, which have been acquired from the guide manipulating portion 7, the distal-end angle of the distal-end curvable portion acquired from the angle input portion 5, and the results of calculating the position and the speed by the speed/position calculation unit of the drive unit 2. Examples of the configuration and control of the control apparatus 4 are described later.

(Configuration Example of Continuum Robot)

Figure 2:
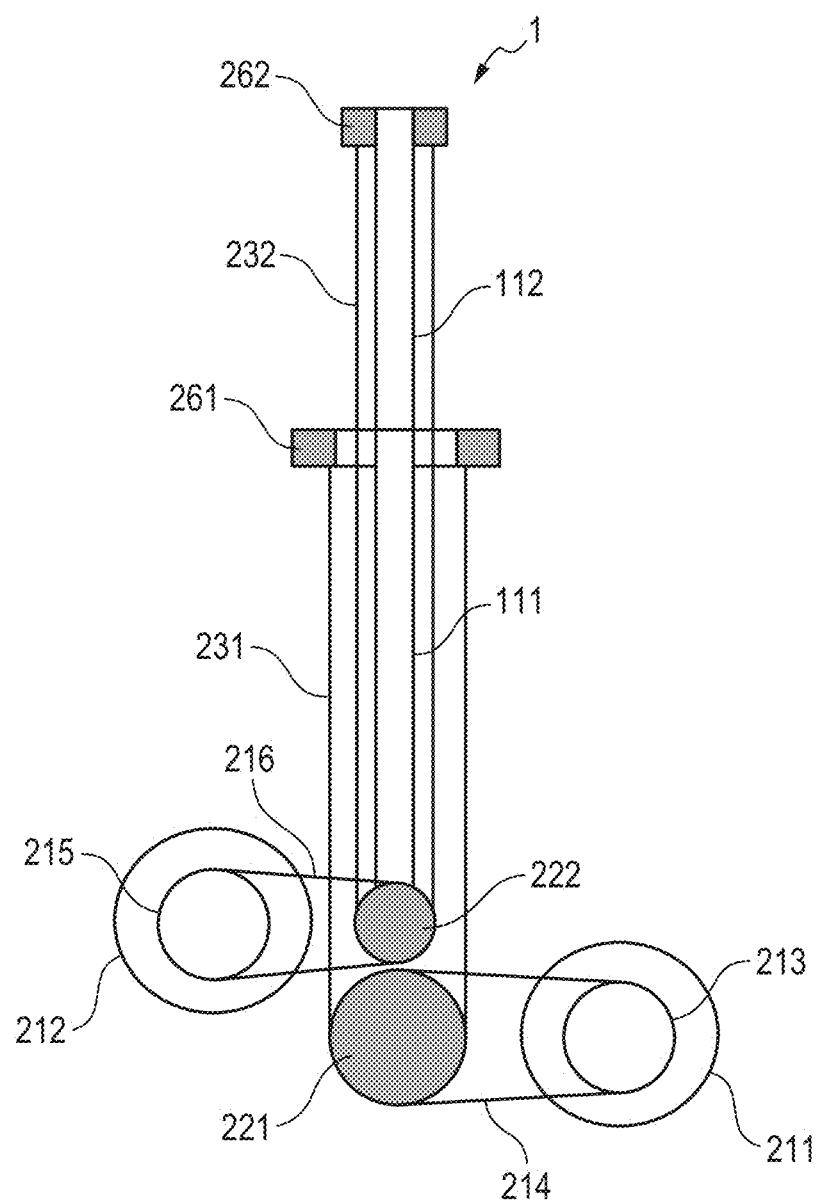
FIG. 2 is a schematic diagram for illustrating a configuration example of a continuum robot.

Next, a configuration example of the continuum robot 1 is described. FIG. 2 is a schematic diagram for illustrating a configuration example of the continuum robot 1. The continuum robot 1 in the first embodiment includes, as an example of the plurality of curvable portions, two curvable portions of a first curvable portion 111 and a second curvable portion 112. In the first embodiment, the first curvable portion 111 is set as the proximal-end curvable portion, and the second curvable portion 112 is set as the distal-end curvable portion. The first curvable portion 111 and the second curvable portion 112 are capable of being curved in an arc shape, and are capable of having the postures changed independently of each other.

A first wire fixing portion 261 is provided at the distal end of the first curvable portion 111, and one end portion of a first wire 231 being a drive transmission mechanism is fixed to the first wire fixing portion 261. The first wire 231 is provided along the first curvable portion 111. The other end portion of the first wire 231 is drawn into the drive unit 2 to be coupled to a first pulley 221 provided inside the drive unit 2. The first pulley 221 is rotated by the driving force of a first angle control motor 211 being an example of the posture changing unit provided inside the drive unit 2. In the first embodiment, a first belt 214 is wound around the first pulley 221 and an output shaft 213 of the first angle control motor 211 so that the rotation of the output shaft 213 of the first angle control motor 211 is transmitted to the first pulley 221 via the first belt 214.

Similarly, a second wire fixing portion 262 is provided at the distal end of the second curvable portion 112, and one end portion of a second wire 232 being a drive transmission mechanism is fixed to the second wire fixing portion 262. The second wire 232 is provided along the first curvable portion 111 and the second curvable portion 112 so as to pass through a hole formed in the first wire fixing portion 261 in an intermediate portion in the longitudinal axial direction. The other end portion of the second wire 232 is drawn into the drive unit 2 to be coupled to a second pulley 222 provided inside the drive unit 2. The second pulley 222 is rotated by the driving force of a second angle control motor 212 being an example of the posture changing unit provided inside the drive unit 2. In the first embodiment, a second belt 216 is wound around the second pulley 222 and an output shaft 215 of the second angle control motor 212 so that the rotation of the output shaft 215 of the second angle control motor 212 is transmitted to the second pulley 222 via the second belt 216.

With such a configuration, the posture of the first curvable portion 111 is changed in accordance with the rotation angle of the output shaft 213 of the first angle control motor 211 being an example of the posture changing unit. In the same manner, the posture of the second curvable portion 112 is changed in accordance with the rotation angle of the output shaft 215 of the second angle control motor 212. In this manner, the first curvable portion 111 and the second curvable portion 112 are both capable of being curved, and are capable of being curved in an arc shape by the actions of the first angle control motor 211 and the second angle control motor 212, which are the examples of the posture changing unit, respectively. A driving force transmission mechanism for transmitting the rotational power of the first angle control motor 211 to the first pulley 221 and a driving force transmission mechanism for transmitting the rotational power of the second angle control motor 212 to the second pulley 222 are not limited to the above-mentioned configurations. In short, it suffices that the rotation angle of the first pulley 221 is uniquely determined from the rotation angle of the output shaft 213 of the first angle control motor 211, and that the rotation angle of the second pulley 222 is uniquely determined from the rotation angle of the output shaft 215 of the second angle control motor 212.

In the first embodiment, the configuration in which the continuum robot 1 includes the first wire 231 and the second wire 232 is taken as an example, but this configuration is obtained by simplifying the continuum robot 1 for the sake of convenience of description, and the continuum robot 1 may include a wire other than those wires. For example, in addition to the second wire 232, the continuum robot 1 may include a fixed wire provided along the first curvable portion 111 and the second curvable portion 112 and fixed to both the first wire fixing portion 261 and the second wire fixing portion 262. With such a configuration, it is possible to three-dimensionally curve each curvable portion. In the configuration illustrated in FIG. 2, the first wire fixing portion 261 has a diameter larger than that of the second wire fixing portion 262, but the configuration is not limited thereto. For example, the first wire fixing portion 261 and the second wire fixing portion 262 may be set to have the same diameter so that the second wire 232 fixed to the second wire fixing portion 262 is inserted to pass through a hole formed in the first wire fixing portion 261. In another case, the first wire 231 may be formed as a plurality of wires driven independently of one another. The same applies to the second wire 232.

(Model of Continuum Robot)

Now, a model used for controlling the follow-the-leader control of the continuum robot 1 and the advancing/reversing action of the drive unit 2 is described. In the first embodiment, a relationship between a distal-end angle $\theta_1$ being an example of the posture of the first curvable portion 111 and the rotation angle of the output shaft 213 of the first angle control motor 211 and a relationship between a distal-end angle $\theta_2$ being an example of the posture of the second curvable portion 112 and the rotation angle of the output shaft 215 of the second angle control motor 212 are defined through use of the model of the continuum robot 1. Then, the control apparatus 4 uses those relationships defined through use of the model to perform the follow-the-leader control of the continuum robot 1 and the speed control of the advancing/reversing action of the drive unit 2.

In order to provide the model, the continuum robot 1 to be controlled in the first embodiment is assumed to satisfy the following four conditions (1) to (4).

(1) The first curvable portion 111 has a constant curvature radius over the total length in the longitudinal axial direction, and the second curvable portion 112 also has a constant curvature radius over the total length in the longitudinal axial direction.

(2) The first curvable portion 111 has a neutral plane $N_1$ located at the center of the first curvable portion 111, and the second curvable portion 112 has a neutral plane $N_2$ located at the center of the second curvable portion 112.

(3) The first wire 231 and the second wire 232 do not expand or contract (extraction/contraction thereof is not taken into consideration).
(4) The first curvable portion 111 and the second curvable portion 112 have the same longitudinal axial dimension.

Figure 3:
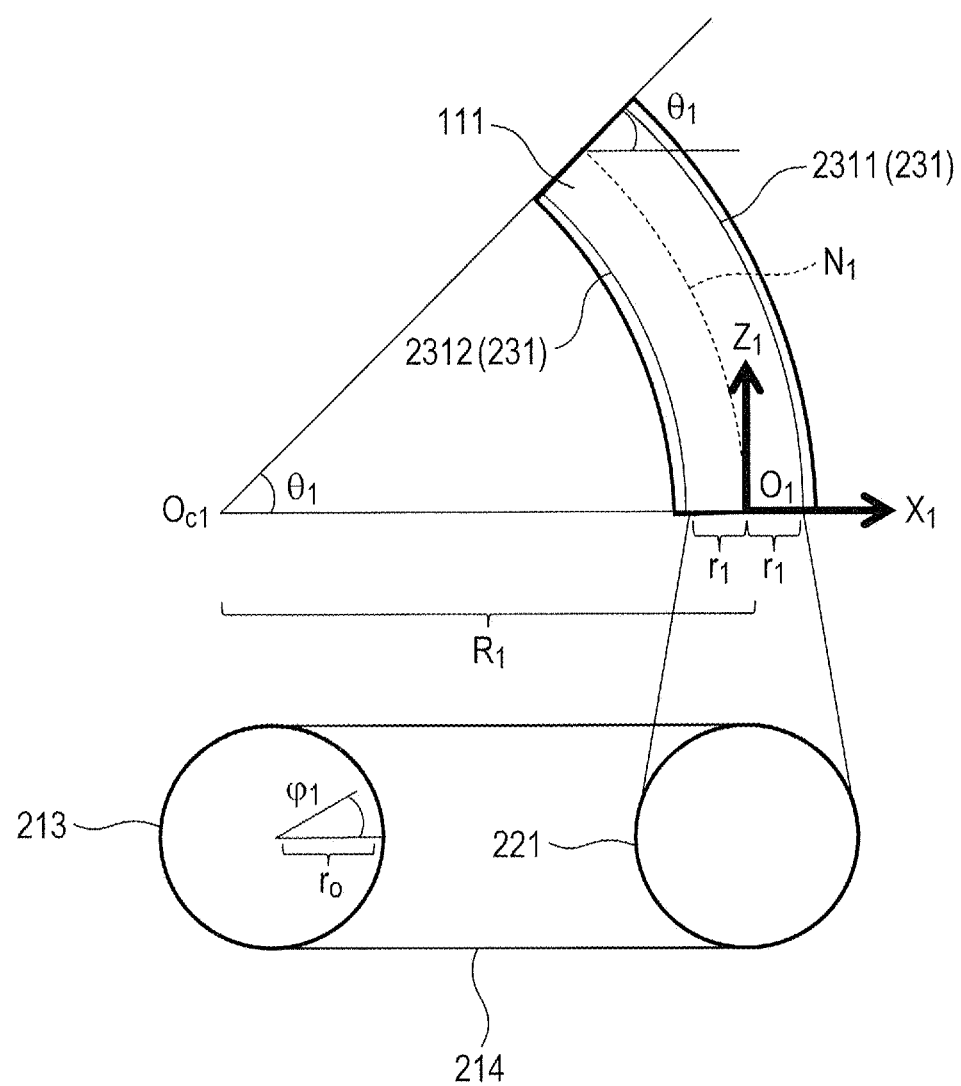
FIG. 3 is a schematic diagram for illustrating a model of a first curvable portion of the continuum robot.

First, the model of the first curvable portion 111 is described. FIG. 3 is a schematic diagram for illustrating the model of the first curvable portion 111. As illustrated in FIG. 3, the proximal end of the first curvable portion 111 is set as an original $O_1$, the moving direction of the advancing action of the drive unit 2 is set as a $Z_1$ axis, and an axis perpendicular to the $Z_1$ axis in a plane in which the first curvable portion 111 is changed in posture (changed in angle) is set as an $X_1$ axis. The distal-end angle $\theta_1$ of the first curvable portion 111 is an angle formed between the $X_1$ axis and a straight line passing along the distal end of the first curvable portion 111 perpendicularly to the center line (neutral plane $N_1$). A rotation angle $\varphi_1$ represents the rotation angle of the output shaft 213 of the first angle control motor 211. A distance $r_1$ represents a distance between the neutral plane $N_1$ of the first curvable portion 111 and the first wire 231. Under the condition (1), the neutral plane $N_1$ of the first curvable portion 111 is an arc, and the central angle of the arc is equal to the distal-end angle $\theta_1$ of the first curvable portion 111. Under the condition (2), assuming that the neutral plane $N_1$ has a length $L_c$ and a distance between the center of curvature of the arc and the neutral plane $N_1$ of the first curvable portion 111 is $R_1$, the distal-end angle $\theta_1$ of the first curvable portion 111 is expressed by Mathematical Expression (1).

$\theta_1 = L_c/R_1$  Mathematical Expression (1)

In this case, of the first wire 231, a length $L_{1o}$ of a segment (referred to as "outer segment 2311" for the sake of convenience of description) located outside the neutral plane $N_1$ of the first curvable portion 111 is expressed by Mathematical Expression (2) under the condition (3).

$L_{1o} = (R_1 + r_1)\theta_1$  Mathematical Expression (2)

When the distal-end angle $\theta_1$ of the first curvable portion 111 is 0, the length $L_c$ of the neutral plane $N_1$ of the first curvable portion 111 and the length $L_{1o}$ of the first wire 231 agree with each other. Therefore, a driving amount $\Delta L_{1o}$ of the outer segment 2311 of the first wire 231, which is required for changing the distal-end angle of the first curvable portion 111 from 0 to $\theta_1$, is expressed by Mathematical Expression (3).

$\Delta L_{1o} = L_{1o} - L_c = r_1\theta_1$  Mathematical Expression (3)

Similarly, of the first wire 231, a length $L_{1i}$ of a segment (referred to as "inner segment 2312 for the sake of convenience of description) located inside (side closer to the center of curvature) the neutral plane $N_1$ of the first curvable portion 111 is expressed by Mathematical Expression (4).

$L_{1i} = (R_1 - r_1)\theta_1$  Mathematical Expression (4)

Therefore, a driving amount $\Delta L_{1i}$ of the inner segment 2312 of the first wire 231, which is required for changing the distal-end angle of the first curvable portion 111 from 0 to $\theta_1$, is expressed by Mathematical Expression (5).

$\Delta L_{1i} = L_{1i} - L_c = -r_1\theta_1$  Mathematical Expression (5)

Mathematical Expression (3) and Mathematical Expression (5) indicate that the driving amounts of the outer segment 2311 and the inner segment 2312 of the first wire 231 have the same size and opposite directions. When the rotation angle of the output shaft 213 of the first angle control motor 211 is changed from 0 to $\varphi_1$, the driving amount $\Delta L_{1o}$ of the outer segment 2311 of the first wire 231 and the driving amount $\Delta L_{1i}$ of the inner segment 2312 of the first wire 231 are expressed by Mathematical Expression (6). In Mathematical Expression (6), $r_o$ represents a radius of the output shaft 213 of the first angle control motor 211.

$r_o\varphi_1 = \Delta L_{1o} = -\Delta L_{1i}$  Mathematical Expression (6)

In accordance with those mathematical expressions, the relationship between the distal-end angle $\theta_1$ of the first curvable portion 111 and the rotation angle $\varphi_1$ of the output shaft 213 of the first angle control motor 211 is expressed by Mathematical Expression (7).

$\theta_1 = (r_o/r_1)\varphi_1$  Mathematical Expression (7)

Figure 4:
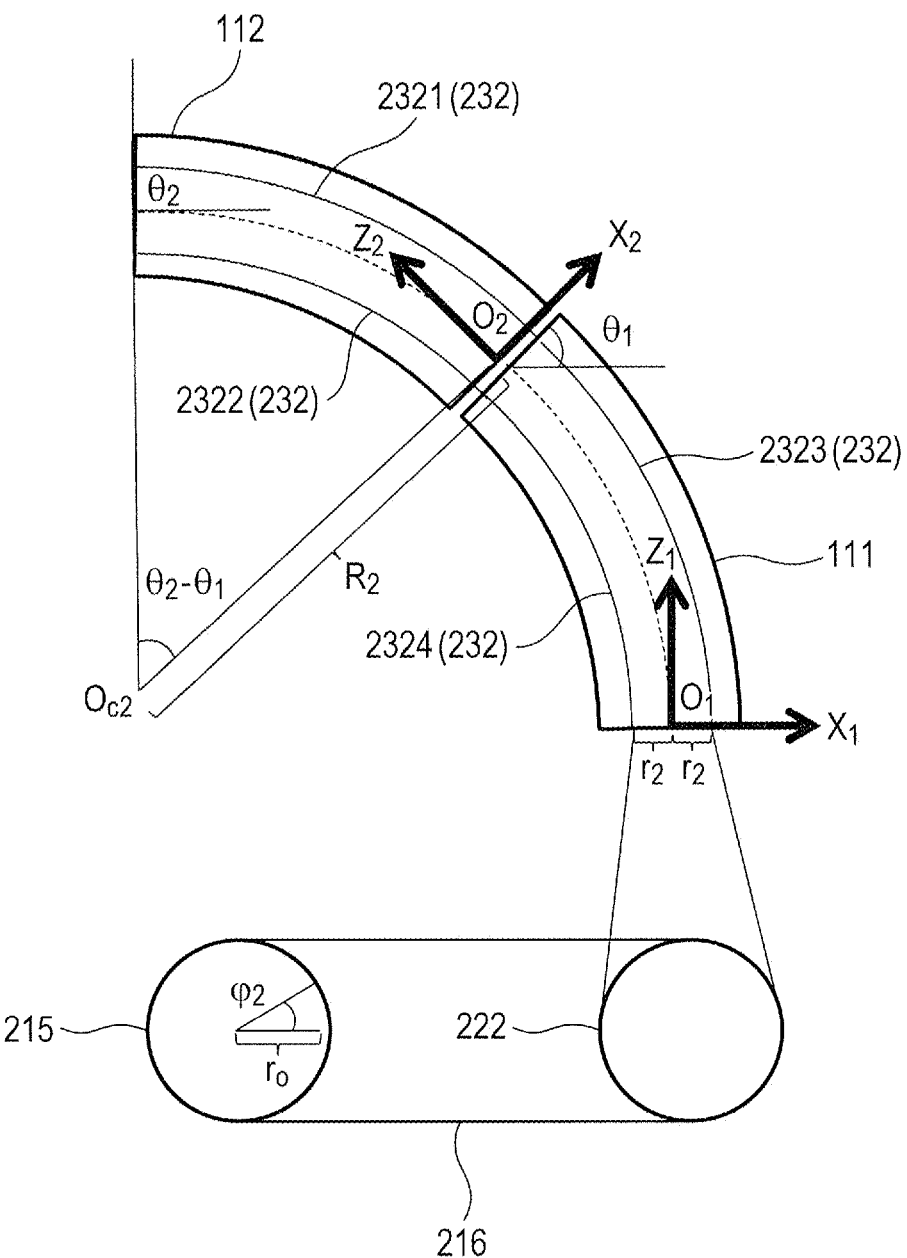
FIG. 4 is a schematic diagram for illustrating a model of a second curvable portion of the continuum robot.

Next, the relationship between the distal-end angle $\theta_2$ of the second curvable portion 112 and the rotation angle $\varphi_2$ of the output shaft 215 of the second angle control motor 212 is described. FIG. 4 is a schematic diagram for illustrating a model of the second curvable portion 112 of the continuum robot 1. In FIG. 4, the first angle control motor 211 and the first pulley 221 are omitted. The distal-end angle $\theta_2$ of the second curvable portion 112 is an angle formed between the $X_1$ axis and a straight line passing along the distal end of the second curvable portion 112 perpendicularly to the center line (neutral plane $N_2$). As illustrated in FIG. 4, the proximal end of the second curvable portion 112 is set as an original $O_2$, the longitudinal axial direction of the second curvable portion 112 is set as a $Z_2$ axis, and an axis perpendicular to the $Z_2$ axis in a plane in which the second curvable portion 112 is driven is set as an $X_2$ axis. In the first embodiment, the first curvable portion 111 and the second curvable portion 112 are changed in posture in the same plane, and hence an $X_1$-$Z_1$ plane and an $X_2$-$Z_2$ plane agree with each other.

Under the conditions (2) and (3), even when a curvature radius $R_2$ of the second curvable portion 112 is changed, the lengths of the neutral plane $N_1$ of the first curvable portion 111 and the first wire 231 are not changed. Therefore, even when the curvature radius $R_2$ of the second curvable portion 112 is changed, Mathematical Expression (7) is established for the first curvable portion 111. Under the condition (1), the neutral plane $N_2$ of the second curvable portion 112 is also an arc in the same manner as in the case of the first curvable portion 111. Under the condition (4), the length of the second curvable portion 112 is equal to the length $L_c$ of the neutral plane $N_2$. Therefore, assuming that the distal-end angle of the second curvable portion 112 with respect to the $X_1$ axis is $\theta_2$ and a distance between the neutral plane $N_2$ and the center of the arc is $R_2$, Mathematical Expression (8) is established. In Mathematical Expression (8), the left-hand side indicates the central angle of the arc of the second curvable portion 112.

$\theta_1 - \theta_2 = L_c/R_2$  Mathematical Expression (8)

Of the second wire 232, a length $L_{22o}$ of a segment 2321 along the second curvable portion 112 within a segment (referred to as "outer segment" for the sake of convenience of description) located outside the neutral plane $N_2$ in the curvature radius direction is expressed by Mathematical Expression (9). In Mathematical Expression (9), $r_2$ represents a distance between the neutral plane $N_2$ of the second curvable portion 112 and the second wire 232.

$L_{22o} = (R_2 + r_2)(\theta_1 - \theta_2)$  Mathematical Expression (9)

Of the second wire 232, a length $L_{21o}$ of a segment 2323 along the first curvable portion 111 within a segment (referred to as "outer segment" for the sake of convenience of description) located outside the neutral plane $N_1$ of the first curvable portion 111 in the curvature radius direction is expressed by Mathematical Expression (10) in the same manner as in the case of the first curvable portion 111 expressed by Mathematical Expression (2).

$$L_{21o}=(R_1+r_2)\theta_1 \qquad \text{Mathematical Expression (10)}$$

Therefore, a sum $L_{2o}$ of the outer segments 2321 and 2323 of the second wire 232 is expressed by Mathematical Expression (11) in accordance with Mathematical Expression (9) and Mathematical Expression (10).

$$\begin{aligned}L_{2o} &= L_{21o} + L_{22o} \qquad \text{Mathematical Expression (11)}\\ &= R_2(\theta_1-\theta_2)+R_1\theta_1+r_2\theta_2\\ &= 2L_c + r_2\theta_2\end{aligned}$$

Therefore, a driving amount $\Delta L_{2o}$ of the outer segment of the second wire 232, which is exhibited when the distal-end angle of the second curvable portion 112 is $\theta_2$, is expressed by Mathematical Expression (12).

$$\Delta L_{2o}=L_{2o}-2L_c=r_2\theta_2 \qquad \text{Mathematical Expression (12)}$$

In the same manner, of the second wire 232, lengths $L_{22i}$ and $L_{21i}$ of segments (hereinafter referred to as "inner segments 2322 and 2324") located inside the neutral plane $N_2$ in the curvature radius direction are expressed by Mathematical Expression (13) and Mathematical Expression (14), respectively. In addition, of the second wire 232, a driving amount $\Delta L_{2i}$ of the inner segments 2322 and 2324 is expressed by Mathematical Expression (15).

$$L_{22i}=(R_2-r_2)(\theta_2-\theta_1) \qquad \text{Mathematical Expression (13)}$$

$$L_{21i}=(R_1-r_2)\theta_1 \qquad \text{Mathematical Expression (14)}$$

$$\Delta L_{2i}=(L_{22i}+L_{21i})-2L_c=-r_2\theta_2 \qquad \text{Mathematical Expression (15)}$$

Therefore, when the rotation angle of the output shaft 215 of the second angle control motor 212 is changed from 0 to $\varphi_2$, the relationship between the rotation angle $\varphi_2$ of the output shaft 215 and the distal-end angle $\theta_2$ of the second curvable portion 112 is expressed by Mathematical Expression (16). In Mathematical Expression (16), $r_o$ represents the radius of the output shaft 215 of the second angle control motor 212.

$$\theta_2=(r_o/r_2)\varphi_2 \qquad \text{Mathematical Expression (16)}$$

As described above, the relationship between the rotation angle $\varphi_1$ of the output shaft 213 of the first angle control motor 211 and the distal-end angle $\theta_1$ of the first curvable portion 111 is defined from the model of the continuum robot 1. In the same manner, the relationship between the rotation angle $\varphi_2$ of the output shaft 215 of the second angle control motor 212 and the distal-end angle $\theta_2$ of the second curvable portion 112 is defined. The control apparatus 4 uses those relationships to perform the follow-the-leader control of the continuum robot 1 and the control of the advancing/reversing action of the drive unit 2.

The above description is directed to the continuum robot 1 including the two curvable portion provided so as to be connected in series in the longitudinal axial direction, but there are no limitations imposed on the number of curvable portions. The relationship between the rotation angle of the output shaft of the angle control motor and the distal-end angle of the distal-end curvable portion can also be defined in the same manner for a continuum robot including three or more curvable portions provided so as to be connected in series in the longitudinal axial direction. That is, under the conditions (1) to (4), the distal-end angle $\theta_i$ of an i-th curvable portion depends only on the rotation angle $\varphi_i$ of the output shaft of an i-th angle control motor configured to drive an i-th curvable portion. In addition, the relationship between the rotation angle $\varphi_i$ of the output shaft of the i-th angle control motor and the distal-end angle $\theta_i$ of the i-th curvable portion is expressed by Mathematical Expression (17) through use of a distance $r_i$ between a neutral plane $N_i$ of the i-th curvable portion and a wire configured to drive the i-th curvable portion. In Mathematical Expression (17), i represents a positive integer, and is set to 1 in the proximal-end curvable portion.

$$\theta_i=(r_o/r_2)\varphi_i \qquad \text{Mathematical Expression (17)}$$

In the first embodiment, the configuration in which a speed reduction mechanism is not provided between the first angle control motor 211 and the first curvable portion 111 and between the second angle control motor 212 and the second curvable portion 112 is taken as an example. That is, the moving amount ((rotation angle)×(radius)) of the outer peripheral surface of the output shaft 213 of the first angle control motor 211 in its circumferential direction is the same as the driving amount of the first wire 231. In addition, the moving amount ((rotation angle)×(radius)) of the outer peripheral surface of the output shaft 215 of the second angle control motor 212 in its circumferential direction is the same as the driving amount of the second wire 232. However, this disclosure is not limited to such a model. For example, a configuration in which speed reduction mechanisms or boost mechanisms are provided between the first angle control motor 211 and the first curvable portion 111 and between the second angle control motor 212 and the second curvable portion 112 may be employed. In this case, each of the right-hand sides of Mathematical Expression (7), Mathematical Expression (16), and Mathematical Expression (17) may be multiplied by a coefficient corresponding to the speed reduction ratio of the speed reduction mechanism or a boost ratio of the boost mechanism.

(Control Apparatus)

Figure 5:
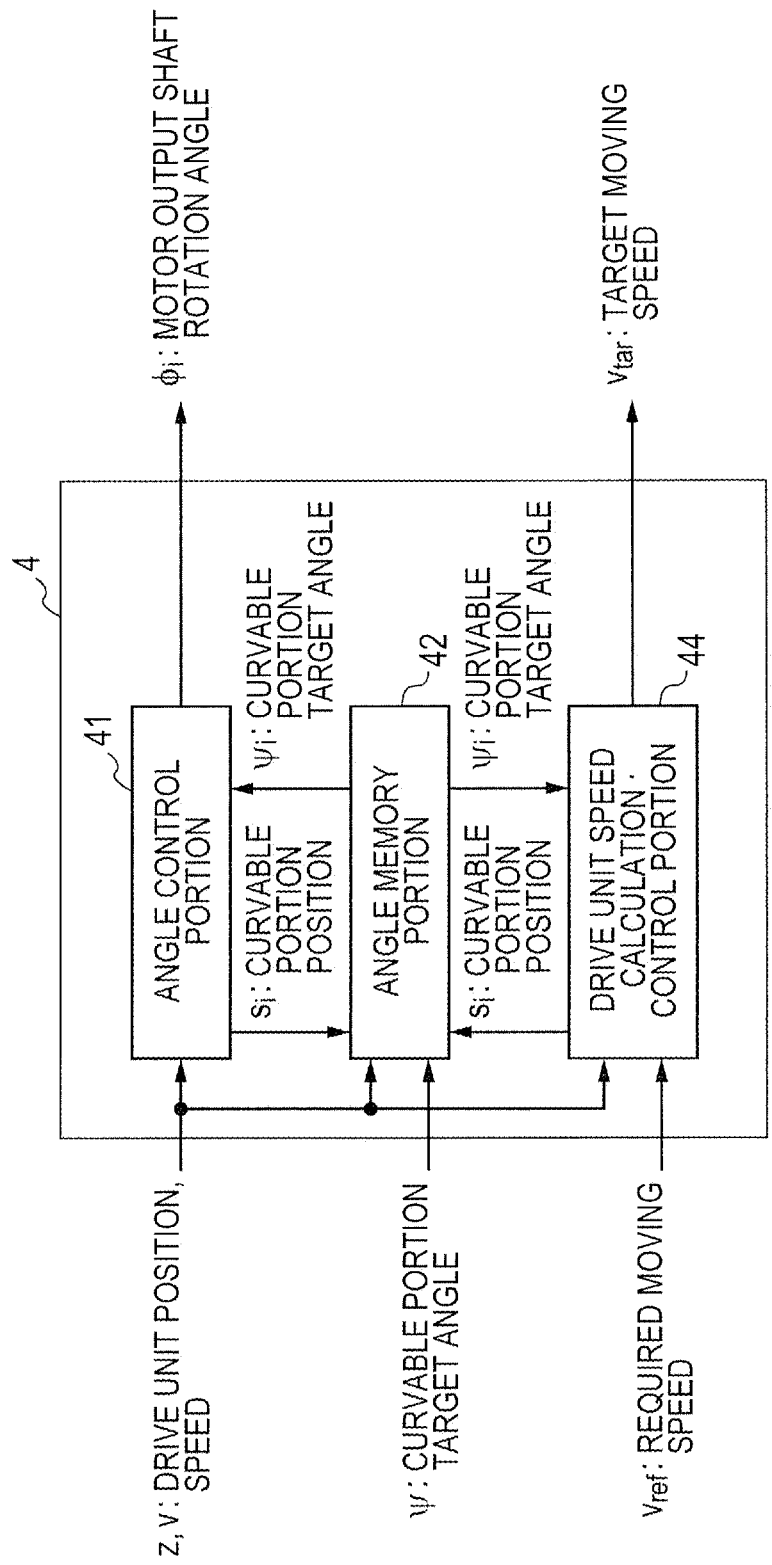
FIG. 5 is a block diagram for illustrating a configuration example of a control apparatus according to the first embodiment.

Next, the control apparatus 4 is described. FIG. 5 is a block diagram for illustrating a configuration example of the control apparatus 4. As illustrated in FIG. 5, the control apparatus 4 includes an angle control unit 41, an angle memory portion 42, and a drive unit speed calculation/control unit 44 being an example of a movable drive control unit. The angle memory portion 42 stores a position z of the drive unit 2, which is acquired from the drive unit 2, and a target angle $\psi$ of the distal end being an example of the target posture of the second curvable portion 112, which is acquired from the angle input portion 5. The angle control unit 41 reads out, from the angle memory portion 42, a target angle $\psi_i$ (target posture) exhibited when the position of the i-th curvable portion (where i is 1 or 2) is $s_i$, and controls the distal-end angles $\theta_1$ and $\theta_2$ of the first curvable portion 111 and the second curvable portion 112, respectively, so that the continuum robot 1 performs the follow-the-leader control. The drive unit speed calculation/control unit 44 calculates a target moving speed of the advancing/reversing action of the drive unit 2. Then, the drive unit speed calculation/control unit 44 controls the movement driving unit 32 so that the moving speed of the advancing/reversing action of the drive unit 2 achieves the calculated target moving speed.

The control apparatus 4 includes a computer including a CPU, a ROM or other such storage medium, and a RAM. A computer program for controlling the drive unit 2 is stored in advance in the ROM or other such storage medium. The CPU of the computer of the control apparatus 4 reads out this computer program stored in the ROM or other such storage medium, and uses the RAM as a work area to execute the computer program. With this configuration, the computer functions as the respective components of the control apparatus 4 to achieve the control of the continuum robot 1 and the speed control of the drive unit 2, which are described later.

(Follow-the-Leader Control)

Now, the follow-the-leader control of the continuum robot 1, which is performed by the control apparatus 4, is described. In FIG. 6A to FIG. 6D, an example of performing the follow-the-leader control when the continuum robot 1 is caused to perform an advancing action along a path having a curved part is illustrated. A path (hereinafter referred to as "insertion/extraction path") for inserting or extracting the continuum robot 1 is assumed to have a width sufficient to advance the continuum robot 1. In each of FIG. 6A to FIG. 6D, the thick solid lines indicate boundaries for defining the insertion/extraction path. In addition, in each of FIG. 6A to FIG. 6D, the broken line indicates the target path of the continuum robot 1, and the control apparatus 4 controls the respective curvable portions of the continuum robot 1 so as to be inserted or extracted (so as to perform an advancing/reversing action) along a target path T described above. The target path T is appropriately determined based on the shape or the like of the insertion/extraction path by, for example, the user. In an exemplary case of using a flexible endoscope, the user sets the target path T based on an image acquired through photographing using the camera 6, or sets the target path T after grasping the insertion/extraction path through MRI examination.

As illustrated in FIG. 6A to FIG. 6D, the insertion/extraction path has a curved part, and hence the target path T also has a curved part. The control apparatus 4 controls the distal-end angle $\theta_1$ of the first curvable portion 111 and the distal-end angle $\theta_2$ of the second curvable portion 112 so as to prevent the first curvable portion 111 and the second curvable portion 112 of the continuum robot 1 from deviating from the target path T even in the curved part of the insertion/extraction path. In other words, the control apparatus 4 controls the distal-end angles $\theta_1$ and $\theta_2$ so as to prevent the plurality of curvable portions of the continuum robot 1 from deviating toward the outside of the insertion/extraction path. In a case where a coordinate axis s is set along the target path T, when each of the curvable portions of the continuum robot 1 is positioned on the target path T, the moving amount of the drive unit 2 in the Z direction and the moving amount of each of the curvable portions in the s direction agree with each other. Therefore, in the first embodiment, a position s is used to indicate a position of each of the curvable portions in its advancing/reversing direction.

Figure 6A:
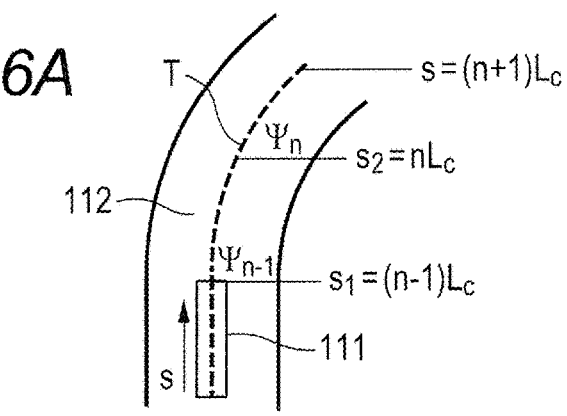
FIG. 6A, FIG. 6B, FIG. 6C, and FIG. 6D are diagrams for illustrating follow-the-leader control for the continuum robot.

FIG. 6A is an illustration of an example of an initial state of the continuum robot 1. As illustrated in FIG. 6A, the distal-end angle $\theta_2$ of the second curvable portion 112 in the initial state is set as $\psi_n$, and a position 52 thereof is set as $nL_c$. In addition, the distal-end angle $\theta_1$ of the first curvable portion 111 in the initial state is set as $\psi_{n-1}$, and a position $s_1$ thereof is set as $(n-1)L_c$. In this case, n represents a positive integer, and $L_c$ represents the longitudinal axial dimension (longitudinal axial dimension of each of the neutral planes $N_1$ and $N_2$) of each of the first curvable portion 111 and the second curvable portion 112.

When the continuum robot 1 is caused to perform an advancing action, the user uses the angle input portion 5 to input a target angle $\psi_{n+1}$ at the distal end, which is an example of the target posture of the second curvable portion 112 exhibited when the second curvable portion 112 reaches the position $(n+1)L_c$. The angle memory portion 42 stores the current positions $(n-1)L_c$ and $nL_c$ of the respective curvable portions, the target position $(n+1)L_c$, the current angles $\psi_{n-1}$ and $\psi_n$ at the distal end, and the target angle $\psi_{n+1}$ at the distal end. The angle control unit 41 reads out the angles $\psi_{n-1}$, $\psi_n$, and $\psi_{n+1}$ stored in the angle memory portion 42. Then, the angle control unit 41 uses Mathematical Expression (18) and Mathematical Expression (19) to calculate the distal-end angles $\theta_1$ and $\theta_2$, which are examples of the target postures of the first curvable portion 111 and the second curvable portion 112, respectively, exhibited when the continuum robot 1 is moved from the initial position by a distance l ($0 \leq l \leq L_c$).

$$\theta_2 = (\psi_{n-1} - \psi_n) l / L_c + \psi_n \qquad \text{Mathematical Expression (18)}$$

$$\theta_1 = (\psi_n - \psi_{n-1}) l / L_c + \psi_{n-1} \qquad \text{Mathematical Expression (19)}$$

Figure 6B:
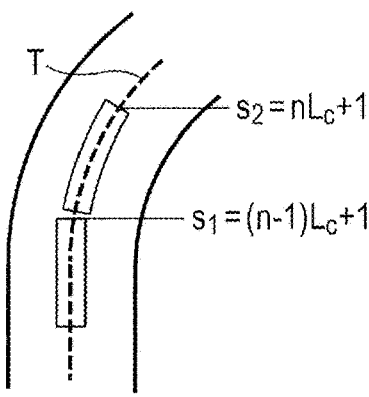
Figure 6C:
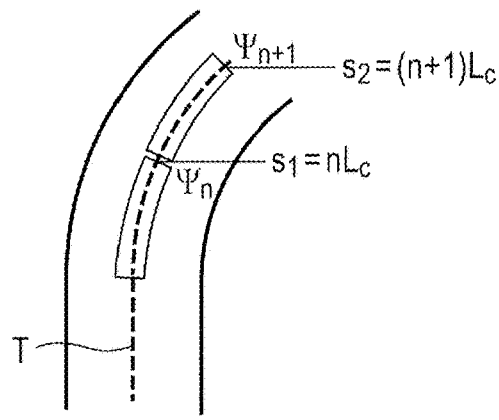
Figure 6D:
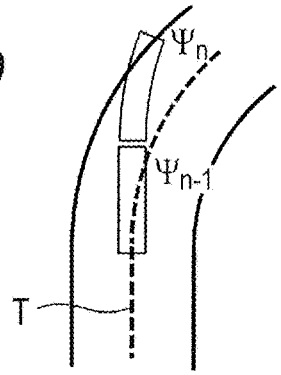

FIG. 6B is an illustration of a state in which the continuum robot 1 has been advanced from the initial state illustrated in FIG. 6A by the distance L (the same distance as the dimensions of the first curvable portion 111 and the second curvable portion 112 in the longitudinal axial direction). As illustrated in FIG. 6B, when the drive unit 2 is advanced by the movement driving unit 32, the continuum robot 1 is accordingly advanced by the distance $L_c$. In this case, the angle control unit 41 uses Mathematical Expression (7) and Mathematical Expression (16) to calculate the target rotation angles $\varphi_1$ and $\varphi_2$ of the output shafts 213 and 215 of the first angle control motor 211 and the second angle control motor 212 from the distal-end angles $\theta_1$ and $\theta_2$, respectively. Then, the angle control unit 41 controls the first angle control motor 211 and the second angle control motor 212 so as to achieve the calculated target rotation angles $\varphi_1$ and $\varphi_2$. As is apparent from Mathematical Expression (18) and Mathematical Expression (19), when the drive unit 2 is advanced from l=0 toward $l=L_c$, the distal-end angle $\theta_1$ of the first curvable portion 111 is continuously changed from $\psi_{n-1}$ to $\psi_n$, and the distal-end angle $\theta_2$ of the second curvable portion 112 is continuously changed from $\psi_n$ to $\psi_{n-1}$. Therefore, as illustrated in FIG. 6C, the posture of the first curvable portion 111 at $s_1 = nL_c$ agrees with the posture of the second curvable portion 112 at the same position.

Each time the continuum robot 1 is advanced by the distance $L_c$ (the same distance as the dimensions of the first curvable portion 111 and the second curvable portion 112 in the longitudinal axial direction), the angle control unit 41 executes the same processing. That is, when a target angle $\psi_{n+2}$ of the second curvable portion 112 at the target position $(n+2)L_c$ is input to advance the continuum robot 1, the angle control unit 41 uses Mathematical Expression (20) and Mathematical Expression (21) to calculate the distal-end angles $\theta_1$ and $\theta_2$. Then, the angle control unit 41 controls the rotation angles of the output shafts 213 and 215 of the first angle control motor 211 and the second angle control motor 212 so as to cause the distal-end angles of those respective curvable portions to agree with the target angles. Mathematical Expression (20) and Mathematical Expression (21) are obtained by substituting n in Mathematical Expression (18) and Mathematical Expression (19), respectively, by n+1.

$$\theta_2 = (\psi_{n+2} - \psi_{n+1}) l / L_c + \psi_{n+1} \qquad \text{Mathematical Expression (20)}$$

$$\theta_1 = (\psi_{n+1} - \psi_n) l / L_c + \psi_n \qquad \text{Mathematical Expression (21)}$$

As is apparent from the fact that Mathematical Expression (18) and Mathematical Expression (21) are the same, the first curvable portion 111 passes so as to follow the path through which the second curvable portion 112 has been advanced from $s_2=nL_c$ to $s_2=(n+1)L_c$. In this manner, the follow-the-leader control is achieved.

Control performed when the continuum robot 1 is caused to perform a reversing action is as follows. The angle control unit 41 controls the distal-end angle $\theta_1$ of the first curvable portion 111 and the distal-end angle $\theta_2$ of the second curvable portion 112 so as to follow the path through which the continuum robot 1 has performed the advancing action. For the sake of convenience of description, the distal-end angle $\theta_2$ of the second curvable portion 112 exhibited when the reversing action is started is set as $\psi_{m+1}$, and the position $s_2$ thereof is set as $(m+1)L_c$. In the same manner, the distal-end angle $\theta_1$ of the first curvable portion 111 is set as $\psi_m$, and the position $s_1$ thereof is set as $mL_c$. In this case, m represents a positive integer that satisfies n<m.

As described above, the angle memory portion 42 stores target angles $\psi_{m-1}$, $\psi_m$, and $\psi_{m+1}$, which are input at the time of the advancing action. In this state, the angle control unit 41 first reads out the target angles $\psi_{m-1}$, $\psi_m$, and $\psi_{m+1}$ from the angle memory portion 42. Then, the angle control unit 41 uses Mathematical Expression (22) and Mathematical Expression (23) to calculate the distal-end angles $\theta_1$ and $\theta_2$, and controls the rotation angles of the output shafts 213 and 215 of the first angle control motor 211 and the second angle control motor 212 so as to agree with those target angles $\psi_{m-1}$, $\psi_m$, and $\psi_{m+1}$.

$$\theta_2=(\psi_m-\psi_{m+1})l/L_c+\psi_{m+1} \quad \text{Mathematical Expression (22)}$$

$$\theta_1=(\psi_{m-1}-\psi_m)l/L_c+\psi_m \quad \text{Mathematical Expression (23)}$$

After that, in the same manner as at the time of the advancing action, each time the continuum robot 1 is reversed by the distance $L_c$ (the same distance as the dimensions of the first curvable portion 111 and the second curvable portion 112 in the longitudinal axial direction), the same processing is repeatedly executed. With this configuration, the second curvable portion 112 performs a reversing action along the path through which the first curvable portion 111 has passed. In this manner, the follow-the-leader control is executed even at the time of the reversing action.

(Speed Control)

Next, the speed control of the advancing/reversing action of the continuum robot 1 is described. In order to perform the insertion or extraction of the continuum robot 1 in a short period of time, it is desired to advance or reverse the drive unit 2 as fast as possible. However, there are physical upper limits to the rotation speeds of the first angle control motor 211 and the second angle control motor 212. This means that a certain amount of time is required until the distal-end angle $\theta_1$ of the first curvable portion 111 and the distal-end angle $\theta_2$ of the second curvable portion 112 agree with the target angles after the first angle control motor 211 and the second angle control motor 212 start to perform the actions. Therefore, when the continuum robot 1 is advanced or reversed (that is, inserted or extracted) at a high speed, the continuum robot 1 may complete being advanced by the distance $L_c$ before the distal-end angle $\theta_1$ of the first curvable portion 111 and the distal-end angle $\theta_2$ of the second curvable portion 112 agree with the target angles in some cases. This raises a fear that the first curvable portion 111 or the second curvable portion 112 may deviate from the target path T and brought into contact with a boundary between the insertion/extraction path and the outside. For example, when the continuum robot system in the first embodiment is applied to a flexible endoscope, there is a fear that the continuum robot 1 may be brought into contact with the inner surface of a body tissue of a subject to be examined.

In view of the foregoing, the control apparatus 4 determines whether or not the distal-end angle $\theta_1$ of the first curvable portion 111 and the distal-end angle $\theta_2$ of the second curvable portion 112 can be caused to agree with the target angles before the continuum robot 1 completes being advanced by the distance $L_c$ in a case where the drive unit 2 is caused to perform an advancing action or a reversing action at the required moving speed $v_{ref}$ input (set) by the volume 72. That is, the control apparatus 4 determines whether or not the continuum robot 1 can be advanced by the distance $L_c$ without deviating from the target path T in the case where the drive unit 2 is caused to perform an advancing/reversing action at the required moving speed $v_{ref}$.

In the first embodiment, the drive unit speed calculation/control unit 44 calculates the maximum value of the moving speed that enables each of the curvable portions of the continuum robot 1 to perform an advancing/reversing action without deviating from the target path T. In the first embodiment, a speed having the "maximum value of the moving speed that enables a curvable portion to perform an advancing/reversing action without deviating from the target path T" is referred to as "followable speed". Then, the drive unit speed calculation/control unit 44 determines whether or not the required moving speed $v_{ref}$ that has been set is equal to or lower than the calculated followable speed (speed having a value equal to or smaller than the maximum value of the moving speed that enables a curvable portion to perform an advancing/reversing action without deviating from the target path T). In a case where the required moving speed $v_{ref}$ that has been set is equal to or lower than the calculated followable speed, the case means that it is possible to prevent the continuum robot 1 from deviating from the target path T even when the continuum robot 1 is advanced or reversed at the required moving speed $v_{ref}$. Therefore, in this case, the drive unit speed calculation/control unit 44 determines that it is possible to perform the follow-the-leader control while preventing the continuum robot 1 from deviating from the target path T even when the continuum robot 1 is advanced or reversed at the required moving speed $v_{ref}$. Then, the drive unit speed calculation/control unit 44 sets the target moving speed of the drive unit 2 (continuum robot 1) to be used by the movement driving unit 32 to the required moving speed $v_{ref}$.

Meanwhile, in a case where the required moving speed $v_{ref}$ that has been set exceeds the calculated the followable speed, the case means that there is a fear that the continuum robot 1 may deviate from the target path T when the continuum robot 1 is advanced or reversed at the required moving speed $v_{ref}$. Therefore, in this case, the drive unit speed calculation/control unit 44 determines that there is a fear that the continuum robot 1 may deviate from the target path T when the continuum robot 1 is caused to perform an advancing/reversing action at the required moving speed $v_{ref}$, and sets the target moving speed to the moving speed equal to or lower than the calculated followable speed. Then, the drive unit speed calculation/control unit 44 controls the movement driving unit 32 to advance or reverse the drive unit 2 the target moving speed set in the above-mentioned manner. According to such a configuration, it is possible to prevent the continuum robot 1 from deviating from the target path T.

There is also a fear that the continuum robot 1 may deviate from the target path T also when the continuum robot 1 is advanced or reversed at a too low moving speed. In addition, when the continuum robot 1 is advanced or reversed at a low speed, much time is required for the insertion or extraction even while the continuum robot 1 is prevented from deviating from the target path T. In view of this, the drive unit speed calculation/control unit 44 may set a threshold value of a lower limit to the target moving speed, and may control the movement driving unit 32 so that the drive unit 2 is advanced or reversed at a moving speed equal to or higher than a speed having the threshold value that has been set. Any threshold value is appropriately set as long as the threshold value is equal to or lower than the followable speed. However, from the viewpoint of reduction in time required for the insertion or extraction, the threshold value is preferred to be as large as possible.

Specific details of the control are as follows. First, a description is given of the moving speed that enables the continuum robot 1 to perform an advancing/reversing action without deviating from the target path T, that is, a condition for the moving speed that enables the continuum robot 1 to perform an advancing/reversing action without deviating from the target path T. When both hand sides of Mathematical Expression (7) are differentiated with respect to time, Mathematical Expression (24) is obtained.

$$\dot{\theta}_1 = (r_o/r_2)\dot{\varphi}_1 \qquad \text{Mathematical Expression (24)}$$

In addition, when Mathematical Expression (19) is differentiated with respect to time, Mathematical Expression (25) is obtained based on the fact that $\psi_n$ and $\psi_{n-1}$ have constant values while the drive unit 2 (continuum robot 1) is performing an advancing action.

$$\dot{\theta}_1 = (\psi_n - \psi_{n-1})v/L_c \qquad \text{Mathematical Expression (25)}$$

In accordance with Mathematical Expression (24) and Mathematical Expression (25), Mathematical Expression (26) is obtained.

$$v = L_c/(\psi_n - \psi_{n-1}) \times r_o/r_1 \times \dot{\varphi}_1 \qquad \text{Mathematical Expression (26)}$$

In accordance with Mathematical Expression (26), the maximum value of a moving speed v that enables the distal-end angle $\theta_1$ of the first curvable portion 111 to agree with the target angle while the continuum robot 1 is advanced by the distance $L_c$, that is, a followable speed $v_{u1}$ of the first curvable portion 111, is expressed by Mathematical Expression (27). In this case, $\omega_{max}$ represents the maximum angular velocity of the output shaft 213 of the first angle control motor 211 that can be output.

$$V_{u1} = L_c/|\psi_n - \psi_{n-1}| \times r_o/r_1 \times \omega_{max} \qquad \text{Mathematical Expression (27)}$$

When the moving speed v of the continuum robot 1 is equal to or lower than the followable speed $v_{u1}$ of the first curvable portion 111, which is calculated by Mathematical Expression (27), it is possible to cause the distal-end angle $\theta_1$ of the first curvable portion 111 to agree with the target angle while the continuum robot 1 is advanced by the distance $L_c$ (before the movement is completed).

In the same manner, in accordance with Mathematical Expression (16) and Mathematical Expression (18), a followable speed $v_{u2}$ of the second curvable portion 112 is expressed by Mathematical Expression (28). When the moving speed v of the continuum robot 1 is equal to or lower than the followable speed $v_{u2}$, which is calculated by Mathematical Expression (28), it is possible to cause the distal-end angle $\theta_2$ of the second curvable portion 112 to agree with the target angle while the continuum robot 1 is advanced by the distance $L_c$ (before the movement is completed). In this case, $\omega_{max}$ represents the maximum angular velocity of the output shaft 215 of the second angle control motor 212 that can be output.

$$V_{u2} = L_c/|\psi_n - \psi_{n-1}| \times r_o/r_2 \times \omega_{max} \qquad \text{Mathematical Expression (28)}$$

When the calculation is performed in the same manner through use of Mathematical Expression (7), Mathematical Expression (23), Mathematical Expression (16), and Mathematical Expression (22), it is apparent that the followable speeds $v_{u1}$ and $v_{u2}$ of the first curvable portion 111 and the second curvable portion 112, which are exhibited when the continuum robot 1 (drive unit 2) is reversed, are also given by Mathematical Expression (27) and Mathematical Expression (28).

Therefore, in order to prevent both the first curvable portion 111 and the second curvable portion 112 from deviating from the target path T while the continuum robot 1 is moved by the distance $L_c$, it suffices that the moving speed v of the continuum robot 1 has a value equal to or smaller than the smaller value of the followable speeds of the first curvable portion 111 and the second curvable portion 112. However, Mathematical Expression (27) and Mathematical Expression (28) are derived through use of the model, and an error may exist in some cases. When an error exists in the model of the continuum robot 1, there is a fear that the continuum robot 1 may deviate from the target path T. In view of this, in the first embodiment, a value obtained by multiplying the smaller value of the followable speeds $v_{u1}$ and $v_{u2}$ calculated by Mathematical Expression (27) and Mathematical Expression (28) by a coefficient α is calculated in consideration of an error in the model. The coefficient α has a value larger than 0 and equal to or smaller than 1. It suffices that a specific value of the coefficient α is appropriately set based on the size of an error included in the model. For example, it is preferred that the value of the coefficient α become smaller as the error becomes larger and become larger as the error becomes smaller. When the error is negligibly small, it is not required to multiply the value by the coefficient α (the value of the coefficient α may be set to 1).

The drive unit speed calculation/control unit 44 then determines whether or not the calculated value and the required moving speed $v_{ref}$ of the continuum robot 1 (drive unit 2) satisfy the condition expressed by Mathematical Expression (29). That is, the drive unit speed calculation/control unit 44 determines whether or not the required moving speed $v_{ref}$ is equal to or smaller than a value obtained by multiplying the smallest value among the values of the followable speeds of the respective curvable portions by the coefficient α (equal to or smaller than a followable speed obtained in consideration of an error in the model).

$$v_{ref} \leq \alpha \, \min(L_c/|\psi_{n-i+1} - \psi_{n-i}| \times r_o/r_i \times \omega_{max}) \qquad \text{Mathematical Expression (29)}$$

When Mathematical Expression (29) is established, the drive unit speed calculation/control unit 44 sets the target moving speed of the continuum robot 1 (that is, the target moving speed of the drive unit 2 to be used by the movement driving unit 32) to the required moving speed $v_{ref}$. Meanwhile, when Mathematical Expression (29) is not established for the required moving speed $v_{ref}$, the drive unit speed calculation/control unit 44 sets the target moving speed of the drive unit 2 to a value calculated by the right-hand side of Mathematical Expression (29). The value calculated by the right-hand side of Mathematical Expression (29) is the value obtained by multiplying the smallest value among the values of the followable speeds of the respective curvable portions by the coefficient α (that is, the followable speed obtained in consideration of an error in the model). In this manner, the drive unit speed calculation/control unit 44 limits the target moving speed of the drive unit 2 to a speed equal to or smaller than the followable speed (moving speed limiting unit).

The drive unit speed calculation/control unit 44 repeatedly performs the above-mentioned calculation and control each time the drive unit 2 performs an advancing/reversing action by the distance $L_c$. According to such speed control, it is possible to prevent the continuum robot 1 from greatly deviating from the target path T. It is also possible to move the continuum robot 1 at the maximum speed of the moving speed that enables the continuum robot 1 to follow the target path T. Therefore, the time required for inserting or extracting the continuum robot 1 into/from the insertion/extraction path can be inhibited from becoming longer.

(Example of Processing)

Figure 7:
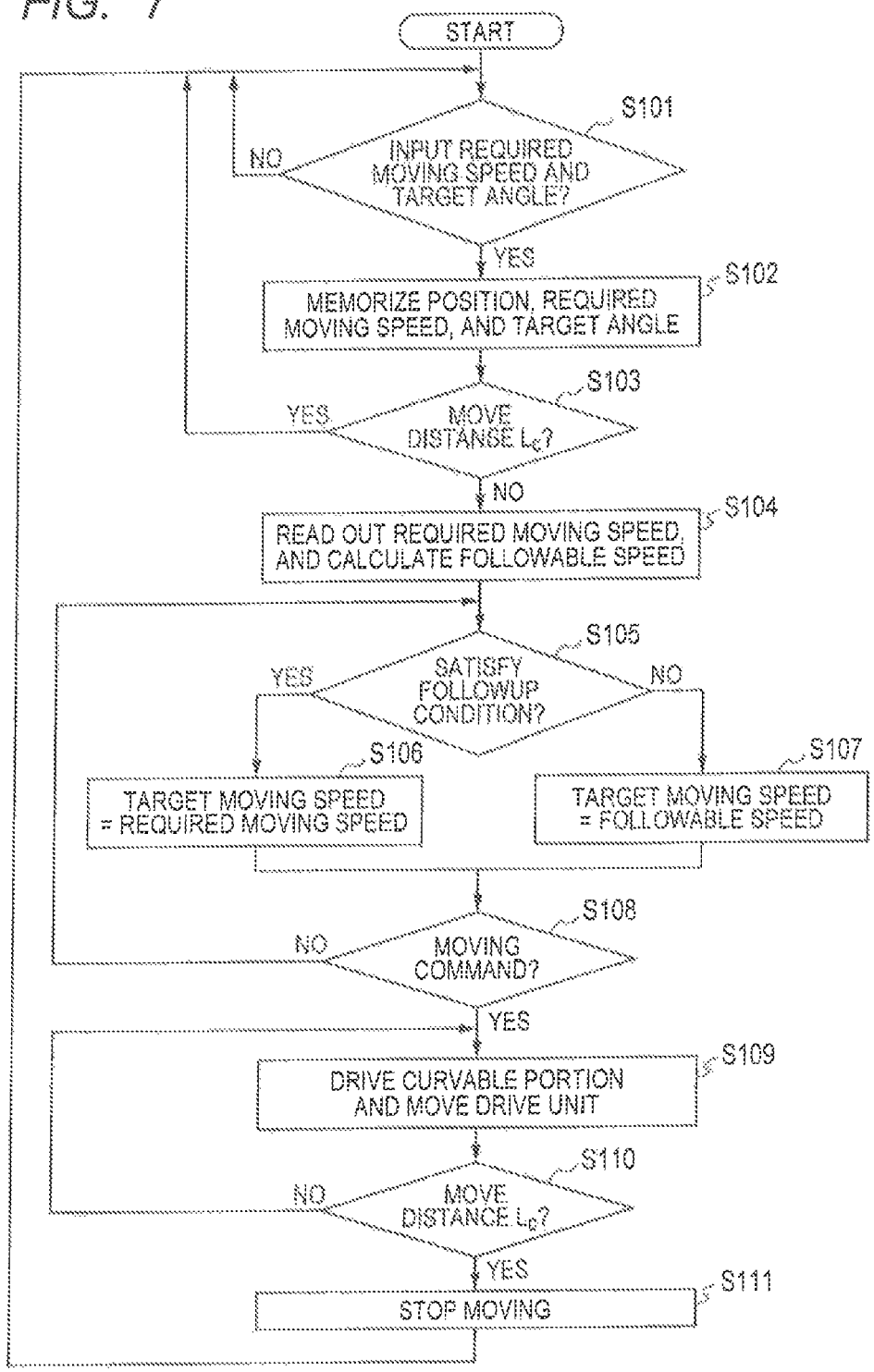
FIG. 7 is a flowchart for illustrating an example of processing executed by the control apparatus.

Next, an example of processing executed by the control apparatus 4 is described. FIG. 7 is a flowchart for illustrating an example of the processing executed by the control apparatus 4. A computer program for executing this processing is stored in advance in the ROM or other such storage medium of the computer of the control apparatus 4. Then, the CPU of the computer reads out this computer program from the ROM or other such storage medium, and uses the RAM as a work area to execute the computer program. With this configuration, the computer functions as the respective components of the control apparatus 4 to achieve the above-mentioned processing.

In Step S101 of "INPUT REQUIRED MOVING SPEED AND TARGET ANGLE?", the drive unit speed calculation/control unit 44 determines whether or not an operation for inputting the required moving speed $v_{ref}$ has been performed on the guide manipulating portion 7 and the target angle has been input to the angle input portion 5. When at least one of those has not been input, the procedure stands by in Step S101. When both have been input, the procedure advances to Step S102.

In Step S102 of "MEMORIZE POSITION, REQUIRED MOVING SPEED, AND TARGET ANGLE", the angle memory portion 42 of the control apparatus 4 acquires the target angle from the angle input portion 5 to store the target angle. The angle memory portion 42 also acquires the position of the drive unit 2 from the speed/position calculation unit of the drive unit 2 to store the position, and acquires the required moving speed $v_{ref}$ from the guide manipulating portion 7 to store the required moving speed $v_{ref}$.

In Step S103 of "MOVE DISTANCE La?", the drive unit speed calculation/control unit 44 determines whether or not the continuum robot 1 has been moved by the distance $L_c$ after the drive unit speed calculation/control unit 44 determines in Step S101 that an operation for inputting the required moving speed $v_{ref}$ has been performed on the guide manipulating portion 7 and an operation for inputting the target angle has been performed on the angle input portion 5. When it is determined that the continuum robot 1 has been moved by the distance $L_c$, the procedure returns to Step S101. When it is determined that the continuum robot 1 has not been moved by the distance $L_c$, the procedure advances to Step S104.

In Step S104 of "READ OUT REQUIRED MOVING SPEED AND CALCULATE FOLLOWABLE SPEED", the drive unit speed calculation/control unit 44 reads out the target angle $\theta_2$ of the distal end of the second curvable portion 112, which is stored in the angle memory portion 42. Then, Mathematical Expression (18), Mathematical Expression (19), Mathematical Expression (22), and Mathematical Expression (23) are used to calculate the target angles of the first curvable portion 111 and the second curvable portion 112, and uses the calculated target angle to calculate the followable speed. The drive unit speed calculation/control unit 44 also reads out the required moving speed $v_{ref}$ stored in the angle memory portion 42.

In Step S105 of "SATISFY FOLLOWUP CONDITION?", the drive unit speed calculation/control unit 44 determines whether or not the required moving speed $v_{ref}$ acquired from the guide manipulating portion 7 satisfies the condition of Mathematical Expression (29). That is, the drive unit speed calculation/control unit 44 determines whether or not the required moving speed $v_{ref}$ is equal to or smaller than a value obtained by multiplying the smallest value of the followable speed among the calculated values of the followable speeds of the respective curvable portions by the coefficient α. The drive unit speed calculation/control unit 44 thus determines whether or not the continuum robot 1 deviates from the target path T when the drive unit 2 is caused to perform an advancing/reversing action at the required moving speed $v_{ref}$. When the condition of Mathematical Expression (29) is satisfied ("Yes"), the procedure advances to Step S106, and when the condition is not satisfied ("No"), the procedure advances to Step S107.

In Step S106 of "TARGET MOVING SPEED=REQUIRED MOVING SPEED", the drive unit speed calculation/control unit 44 sets the target moving speed of the drive unit 2 to be used by the movement driving unit 32 to the required moving speed $v_{ref}$ acquired from the guide manipulating portion 7. Meanwhile, in Step S107 of "TARGET MOVING SPEED=FOLLOWABLE SPEED", the drive unit speed calculation/control unit 44 sets the target moving speed of the drive unit 2 to the value obtained by multiplying the smallest value of the followable speed among the values of the followable speeds of the respective curvable portions by the coefficient α.

In Step S108 of "MOVING COMMAND?", the drive unit speed calculation/control unit 44 determines whether or not there is a command for an advancing action or a command for a reversing action. When there is no command for an advancing action or no command for a reversing action, the procedure returns to Step S105. When there is a command for an advancing action or a command for a reversing action, the procedure advances to Step S109.

In Step S109 of "DRIVE CURVABLE PORTION AND MOVE DRIVE UNIT", the angle control unit 41 drives the first angle control motor 211 and the second angle control motor 212 so as to cause the distal-end angle $\theta_1$ of the first curvable portion 111 and the distal-end angle $\theta_2$ of the second curvable portion 112 to agree with the calculated target angles. That is, the output shafts 213 and 215 of the first angle control motor 211 and the second angle control motor 212 are rotated by the rotation angles defined by Mathematical Expression (7) and Mathematical Expression (16). The drive unit speed calculation/control unit 44 also controls the movement driving unit 32 to cause the drive unit 2 to perform an advancing action or a reversing action at the target moving speed set in Step S106 or Step S107. In this manner, the continuum robot 1 is moved by the distance $L_c$ at the set target moving speed.

In Step S110 of "MOVE DISTANCE $L_c$?", the drive unit speed calculation/control unit 44 determines whether or not the moving distance of the continuum robot 1 has reached the distance $L_c$. When the moving distance of the continuum robot 1 has not reached the distance $L_c$ ("No"), the procedure returns to Step S109 to continue the movement. When the moving distance of the continuum robot 1 has reached the distance $L_c$ ("Yes"), the procedure advances to Step S111.

In Step S111 of "STOP MOVING", the drive unit speed calculation/control unit 44 stops driving the movement driving unit 32 to stop the advancing/reversing action of the drive unit 2 and to stop the advancing/reversing action of the continuum robot 1. Then, the procedure returns to Step S101.

According to the processing described above, when the continuum robot 1 does not deviate from the target path T even while the drive unit 2 is advanced or reversed at the required moving speed $v_{ref}$, the required moving speed $v_{ref}$ is set as the target moving speed to cause the continuum robot 1 to perform an advancing/reversing action. Meanwhile, when there is a fear that the continuum robot 1 may deviate from the target path T at the required moving speed $v_{ref}$, the followable speed is set as the target moving speed to cause the drive unit 2 to perform an advancing/reversing action. The target moving speed set in this case is a speed lower than the required moving speed $v_{ref}$. In this manner, the drive unit speed calculation/control unit 44 functions as a moving speed limiting unit configured to limit the upper limit value of the target moving speed to a value equal to or smaller than the followable speed. According to the above-mentioned configuration, when the continuum robot 1 is advanced or reversed, it is possible to prevent the continuum robot 1 from greatly deviating from the target path T.

In addition, according to the continuum robot system in the embodiment of this disclosure, it is possible to insert or extract the continuum robot 1 at a high speed while preventing the continuum robot 1 from deviating from the target path T. That is, the followable speed is the maximum speed that can prevent the continuum robot 1 from deviating from the target path T, and hence it is possible to suppress reduction in speed of inserting or extracting the continuum robot 1 to a minimum by setting the target moving speed of the continuum robot 1 to the followable speed.

In addition, according to the flexible endoscope to which the continuum robot system in the embodiment of this disclosure is applied, even when the insertion/extraction path (target path T) is complicatedly curved, the distal end of the flexible endoscope (that is, the distal end of the continuum robot 1) can be caused to reach the deep part inside the body of the subject to be examined without being brought into contact with the body tissue of the subject to be examined. This can reduce the load imposed on the subject to be examined. In addition, according to the flexible endoscope to which the continuum robot system in the embodiment of this disclosure is applied, the flexible endoscope can be inserted or extracted at a high speed without being brought into contact with the body tissue of the subject to be examined. As described above, the followable speed is the maximum speed that can prevent the continuum robot 1 from deviating from the target path T, and hence it is possible to suppress the reduction in speed of inserting or extracting the continuum robot 1 to a minimum by setting the target moving speed of the continuum robot 1 to the followable speed. This can reduce the time during which the flexible endoscope is inserted inside the body of the subject to be examined, which can reduce the load imposed on the subject to be examined. It is also possible to reduce the working time of the user (examiner), which can reduce the load imposed on the user (examiner).

Second Embodiment

Next, a second embodiment of this disclosure is described. The same components as those of the first embodiment are denoted by the same reference symbols, and descriptions thereof are omitted. The second embodiment is directed to a configuration in which the user manually advances or reverses the continuum robot 1 in place of the configuration in which the movement driving unit 32 causes the continuum robot 1 to perform an advancing/reversing action together with the drive unit 2. In the same manner as in the first embodiment, the continuum robot 1 is preferred to be advanced or reversed as fast as possible within a range that satisfies the condition for preventing the continuum robot 1 from deviating from the target path T. However, in the configuration in which the user manually advances or reverses the continuum robot 1 (drive unit 2), it is difficult to control the moving speed of the advancing/reversing action with high precision. In view of this, in the second embodiment, when the moving speed of the advancing/reversing action of the continuum robot 1 becomes so high that the continuum robot 1 no longer satisfies the condition for preventing the continuum robot 1 from deviating from the target path T, a brake is applied to the drive unit 2 to reduce the speed of the drive unit 2. With this configuration, when the user advances or reverses the continuum robot 1 (drive unit 2), the continuum robot 1 is prevented from deviating from the target path T.

(Continuum Robot System)

Figure 8:
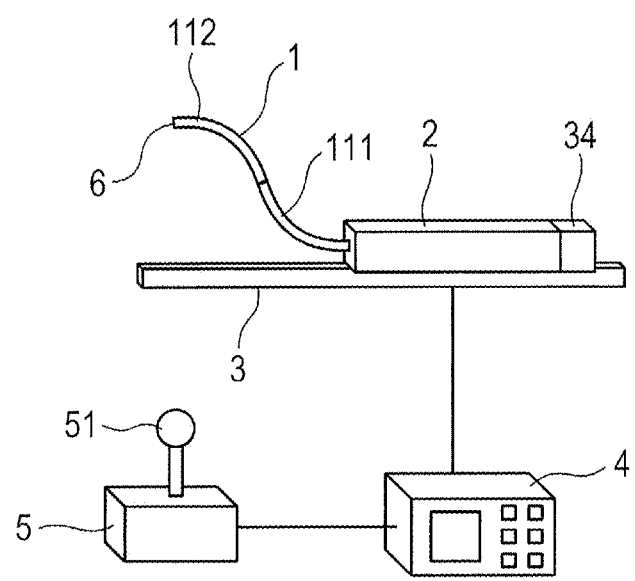
FIG. 8 is a diagram for schematically illustrating a configuration example of a continuum robot system in a second embodiment of this disclosure.

FIG. 8 is a diagram for schematically illustrating a configuration example of a continuum robot system in the second embodiment. As illustrated in FIG. 8, the continuum robot system in the second embodiment includes the continuum robot 1, the drive unit 2, the linear guide 3, the control apparatus 4, the angle input portion 5, and the camera 6. Compared to the continuum robot system in the first embodiment, the continuum robot system in the second embodiment includes a brake portion 34 in place of the movement driving unit 32. The brake portion 34 applies a brake to the drive unit 2 under a brake control unit 43 of the control apparatus 4, which is described later, to lower the speed of an advancing/reversing action. No particular limitations are imposed on the configuration of the brake portion 34, and various known brake mechanisms, for example, an electromagnetic brake, can be employed.

(Control Apparatus)

Figure 9:
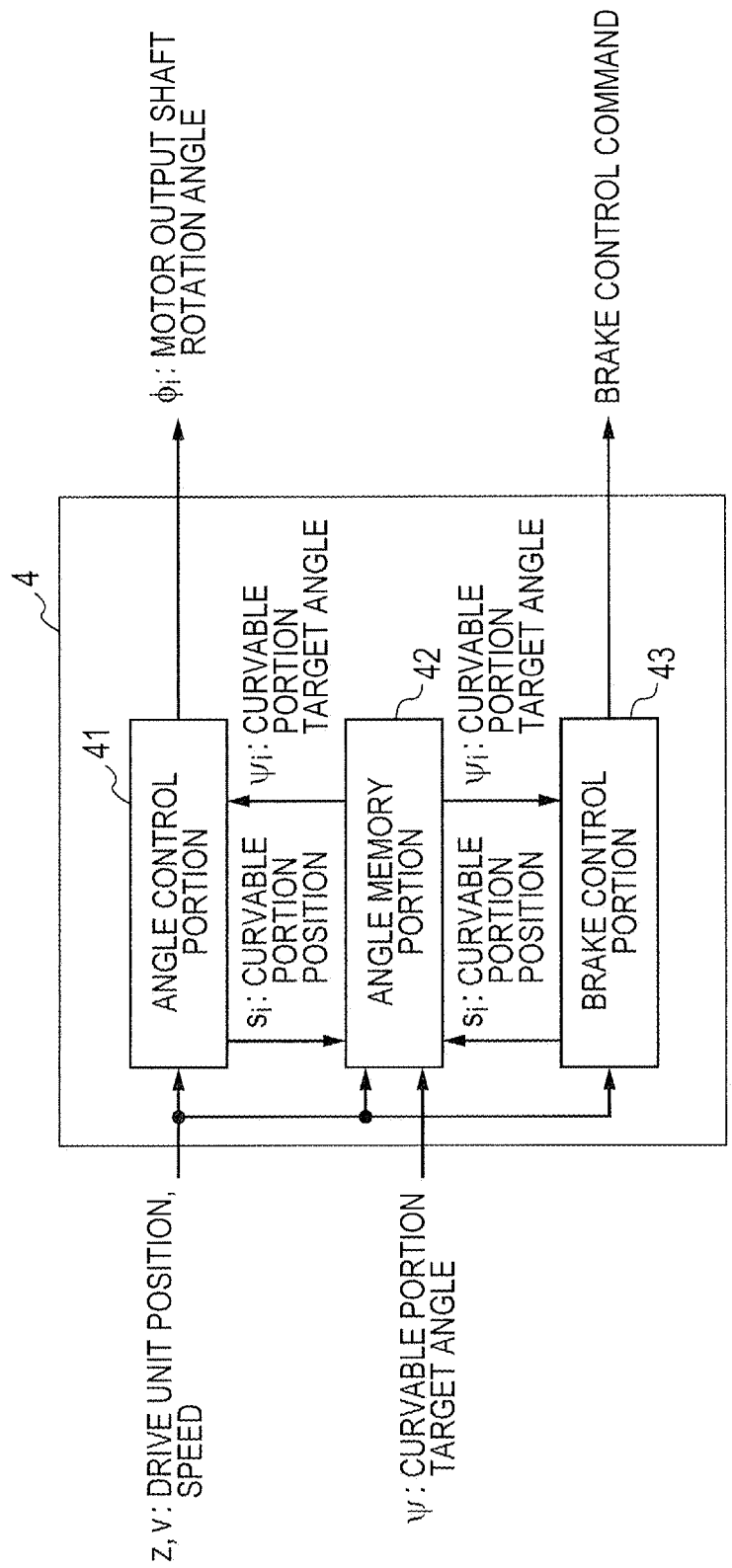
FIG. 9 is a block diagram for illustrating a configuration example of a control apparatus according to the second embodiment.

FIG. 9 is a block diagram for illustrating a configuration example of the control apparatus 4 according to the second embodiment. Compared to the control apparatus 4 according to the first embodiment, the control apparatus 4 according to the second embodiment includes the brake control unit 43 configured to control the brake portion 34 in place of the drive unit speed calculation/control unit 44. Otherwise, the same components can be employed.

As described above, the maximum rotation speeds of the first angle control motor 211 and the second angle control motor 212 are finite, and hence when the speed of the advancing/reversing action of the drive unit 2 becomes higher, there is a fear that the continuum robot 1 may deviate from the target path T. In view of this, the brake control unit 43 calculate, based on the moving speed v of the drive unit 2 and the target angle $\psi_i$ exhibited when the position of the i-th curvable portion is $s_i$, the rotation speeds of the first angle control motor 211 and the second angle control motor 212 that can prevent the continuum robot 1 from deviating from the target path T. When the calculated rotation speed exceeds the maximum rotation speeds of the first angle control motor 211 and the second angle control motor 212, the brake control unit 43 controls the brake portion 34 to reduce the speed of the drive unit 2. With this configuration, the speed of the continuum robot 1 (drive unit 2) is inhibited from exceeding the range that satisfies the condition for preventing the continuum robot 1 from deviating from the target path T.

(Example of Processing of Brake Control Unit)

Now, an example of processing of the brake control unit 43 is described. The followable speeds $v_{u1}$ and $v_{u2}$ of the first curvable portion 111 and the second curvable portion 112, which are exhibited when the continuum robot 1 performs an advancing action by the predetermined distance $L_c$, are expressed by Mathematical Expression (27) and Mathematical Expression (28), respectively, in the same manner as in the first embodiment. When the calculation is performed in the same manner through use of Mathematical Expression (7), Mathematical Expression (23), Mathematical Expression (16), and Mathematical Expression (22), it is apparent that the followable speeds $v_{u1}$ and $v_{u2}$ of the first curvable portion 111 and the second curvable portion 112, which are exhibited when the continuum robot 1 performs a reversing action, are also given by Mathematical Expression (27) and Mathematical Expression (28).

Therefore, the brake control unit 43 determines whether or not the moving speed v is equal to or lower than the followable speeds $v_{u1}$ and $v_{u2}$ calculated by Mathematical Expression (27) and Mathematical Expression (28). When the moving speed v is higher than at least one of the followable speed $v_{u1}$ or $v_{u2}$, the brake control unit 43 controls the brake portion 34 to apply a brake to the drive unit 2 and reduce the speed of the drive unit 2. When the moving speed v is equal to or lower than both the followable speeds $v_{u1}$ and $v_{u2}$ calculated by Mathematical Expression (27) and Mathematical Expression (28), the brake control unit 43 inhibits the activation of the brake portion 34, and deactivates the operation when the brake portion 34 is in operation. In the same manner as in the first embodiment, it may be determined whether or not the moving speed v satisfies Mathematical Expression (29) through use of the coefficient α having a value equal to or smaller than 1 in consideration of an error in the model.

Specifically, the brake control unit 43 acquires the position s of the continuum robot 1, and each time the continuum robot 1 (drive unit 2) is moved by the distance $L_c$, reads out the target angle from the angle memory portion 42 while calculating the followable speeds $v_{u1}$ and $v_{u2}$ through use of Mathematical Expression (27) and Mathematical Expression (28) (speed calculation unit). The position s of the continuum robot 1 may be calculated by the brake control unit 43 through use of the position z of the drive unit 2, and the position z of the drive unit 2 calculated by the angle control unit 41 may be acquired by the brake control unit 43. Then, the brake control unit 43 executes the determination as to whether or not the moving speed v is equal to or smaller than the followable speeds $v_{u1}$ and $v_{u2}$ and the control of the brake portion 34 (activation and deactivation of the brake portion 34) based on the determination result, repeatedly at predetermined control periods. In this case, in one given control period, the moving speed v for the subsequent controlled period is estimated to determine whether or not the estimated moving speed (hereinafter referred to as "estimated moving speed $v_{est}$") is equal to or lower than both the followable speeds $v_{u1}$ and $v_{u2}$.

It is possible to employ a configuration in which, for example, the value of the moving speed v for the one given control period is used as the estimated moving speed $v_{est}$ as it is. In this case, it suffices that the control period is shortened so that the moving speed v for the one given control period and the estimated moving speed $v_{est}$ for the subsequent control period can be recognized as being the same. Further, from a moving speed and an acceleration for one given control period, the estimated moving speed $v_{est}$ for the subsequent control period may be calculated. In this case, the estimated moving speed $v_{est}$ for the subsequent control period can be calculated as (estimated moving speed $v_{est}$ for the subsequent control period)=(moving speed v for the current control period)+(acquired acceleration)×(control period). The brake control unit 43 acquires the acceleration of the drive unit 2 to be used for the above-mentioned calculation from the drive unit 2. In this case, the drive unit 2 includes an acceleration sensor, and can be configured to acquire a result of detecting an acceleration by the acceleration sensor.

According to the configuration described above, the angular velocity of the output shaft 213 of the first angle control motor 211 and the angular velocity of the output shaft 215 of the second angle control motor 212 can be maintained at a velocity equal to or lower than the maximum angular velocity at all times. That is, in the second embodiment, the brake control unit 43 limits the moving speed v of the drive unit 2 to a speed equal to or lower than the followable speed (moving speed limiting unit). In particular, according to the configuration using the estimated moving speed $v_{est}$, it is possible to prevent the braking of the drive unit 2 from being delayed. Therefore, it is possible to cause the distal-end angle $\theta_1$ of the first curvable portion 111 and the distal-end angle $\theta_2$ of the second curvable portion 112 to agree with the target angles, and to prevent the first curvable portion 111 and the second curvable portion 112 from greatly deviating from the target path T. It is also possible to suppress the speed of the drive unit 2 to a minimum speed for preventing the continuum robot 1 from deviating from the target path T.

(Processing of Control Apparatus)

Figure 10:
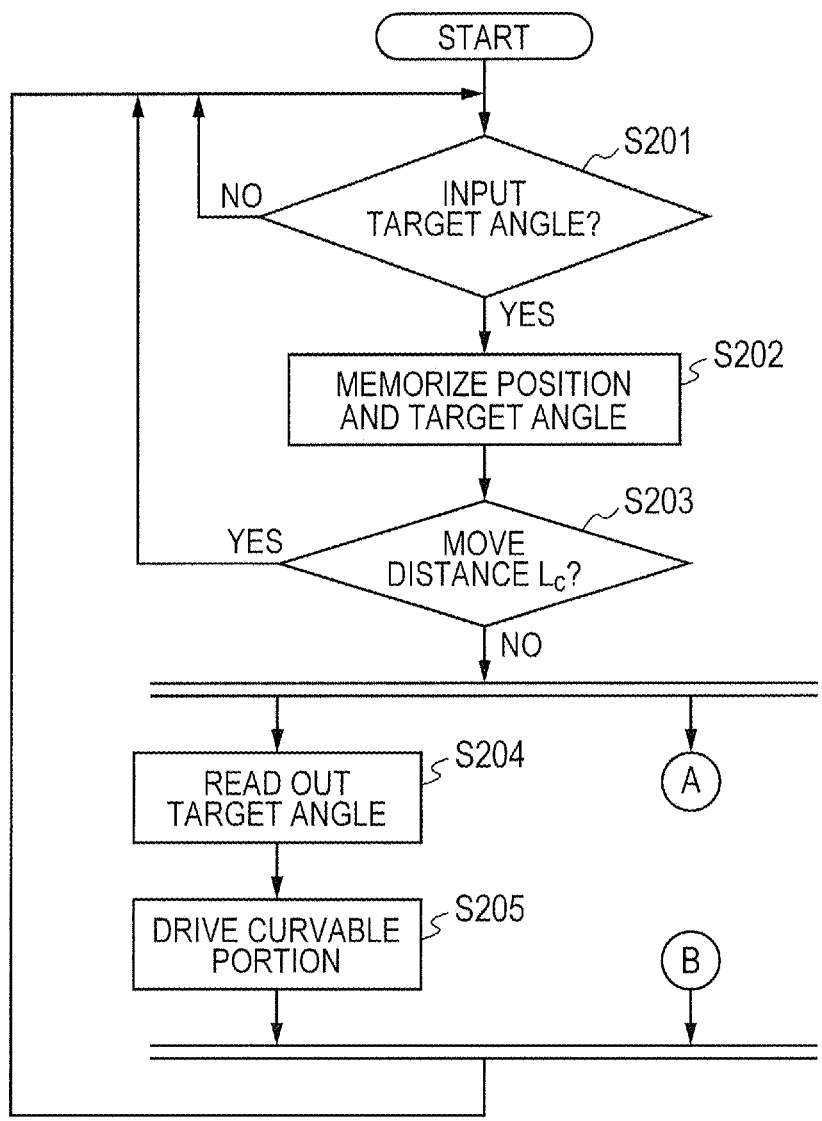
FIG. 10 is a flowchart for illustrating an example of processing executed by the control apparatus.
Figure 11:
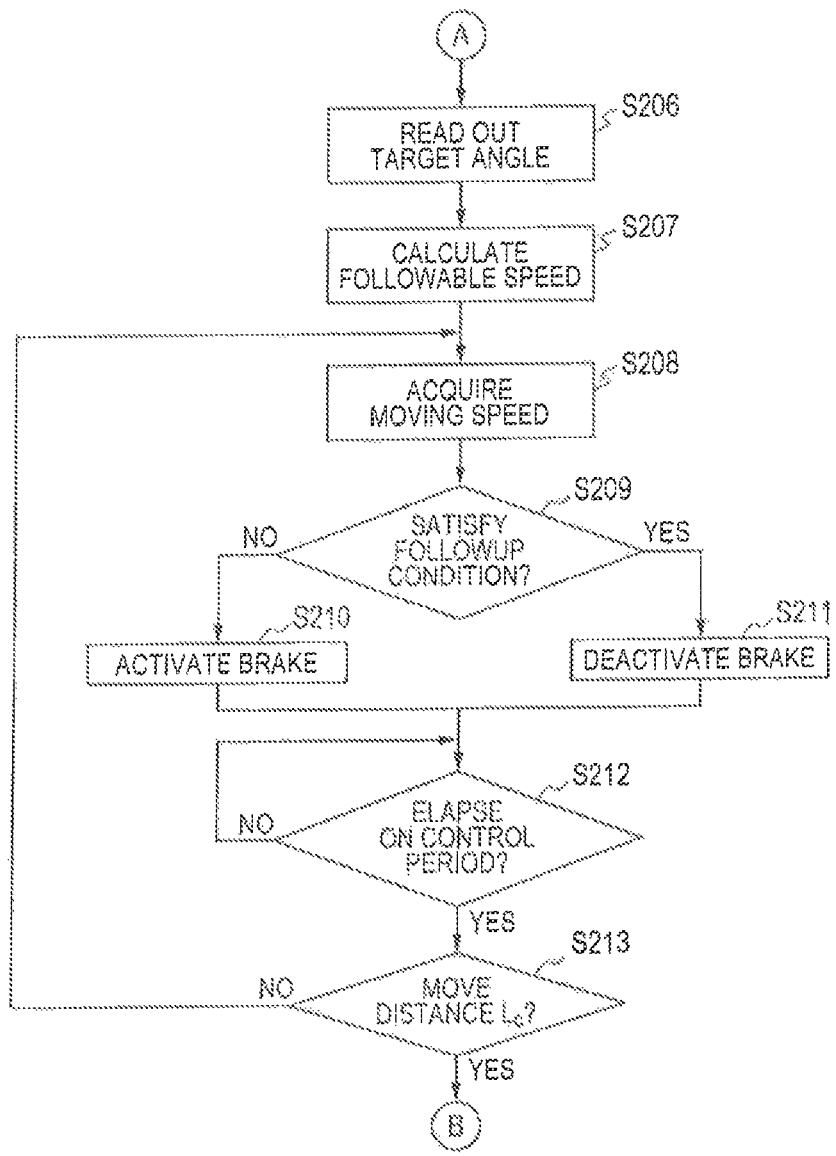
FIG. 11 is a flowchart for illustrating the example of processing executed by the control apparatus.

Next, an example of the processing executed by the control apparatus 4 is described. FIG. 10 and FIG. 11 are flowcharts for illustrating an example of processing executed by the control apparatus 4. FIG. 10 is the flowchart for illustrating the overall processing, and FIG. 11 is the flowchart for illustrating the processing executed between "A" and "B" of FIG. 10.

In Step S201 of "INPUT TARGET ANGLE?", the angle control unit 41 determines whether or not the target angle has been input. When no target angle has been input ("No"), the procedure stands by in Step 201. When the target angle has been input ("Yes"), the procedure advances to Step S202.

In Step S202 of "MEMORIZE POSITION AND TARGET ANGLE", the angle memory portion 42 acquires the position of the continuum robot 1 from the speed/position calculation unit of the drive unit 2 to store the position, and acquires the input target angle from the angle input portion 5 to store the input target angle. Then, the procedure advances to Step S203.

In Step S203 of "MOVE DISTANCE $L_c$?", the brake control unit 43 determines whether or not the drive unit 2 has been moved by the distance $L_c$ after it is determined in Step S201 that the target angle has been input to the angle input portion 5. When it is determined that the drive unit 2 has been moved by the distance $L_c$, the procedure returns to Step S201. When it is determined that the drive unit 2 has not been moved by the distance $L_c$, the procedure advances to Step S204 and Step S206.

In Step S204 of "READ OUT TARGET ANGLE", the angle control unit 41 reads out the target angle stored in the angle memory portion 42. Then, the procedure advances to Step S205.

In Step S205 of "DRIVE CURVABLE PORTION", the angle control unit 41 uses Mathematical Expression (18) and Mathematical Expression (19) to calculate the distal-end angle $\theta_1$ of the first curvable portion 111 and the distal-end angle $\theta_2$ of the second curvable portion 112. The angle control unit 41 also uses Mathematical Expression (16) and Mathematical Expression (17) to calculate the rotation angles $\varphi_1$ and $\varphi_2$ of the output shafts 213 and 215 of the first angle control motor 211 and the second angle control motor 212. Then, the angle control unit 41 controls the first angle control motor 211 and the second angle control motor 212 so as to achieve the calculated rotation angles $\varphi_1$ and $\varphi_2$. The first curvable portion 111 and the second curvable portion 112 are thus driven to cause the distal-end angle $\theta_1$ of the first curvable portion 111 and the distal-end angle $\theta_2$ of the second curvable portion 112 to agree with the target angles.

In Step S206 of "READ OUT TARGET ANGLE", the brake control unit 43 reads out the target angle stored in the angle memory portion 42. Then, the procedure advances to Step S207.

In Step S207 of "CALCULATE FOLLOWABLE SPEED", the brake control unit 43 uses the read target angle to calculate the followable speeds $v_{u1}$ and $v_{u2}$ of the first curvable portion 111 and the second curvable portion 112, respectively. Then, the procedure advances to Step S208.

In Step S208 of "ACQUIRE MOVING SPEED", the brake control unit 43 acquires the current moving speed of the continuum robot 1 (drive unit 2) from the speed/position calculation unit of the drive unit 2. The acquired current moving speed is the moving speed of the continuum robot 1 in the current control period. Then, the procedure advances to Step S209.

In Step S209 of "SATISFY FOLLOWUP CONDITION?", the brake control unit 43 calculates the estimated moving speed $v_{est}$ of the continuum robot 1 in the subsequent control period from the moving speed of the continuum robot 1 in the current control period, which has been acquired in Step S209. Then, the brake control unit 43 determines whether or not the estimated moving speed $v_{est}$ is equal to or lower than both the followable speeds $v_{u1}$ and $v_{u2}$ calculated by Mathematical Expression (27) and Mathematical Expression (28). When the estimated moving speed $v_{est}$ is higher than at least one of the followable speed $v_{u1}$ or $v_{u2}$ ("No"), the procedure advances to Step S210, and when the estimated moving speed $v_{est}$ is equal to or lower than both ("Yes"), the procedure advances to Step S211. It may be determined whether or not a mathematical expression obtained by substituting the left-hand side of Mathematical Expression (29) by the estimated moving speed $v_{est}$ is established. In this case, when this mathematical expression is not established ("No"), the procedure advances to Step S210, and when this mathematical expression is established ("Yes"), the procedure advances to Step S211.

In Step S210 of "ACTIVATE BRAKE", the brake control unit 43 activates the brake portion 34 to apply a brake to the drive unit 2 and reduce the speed of the continuum robot 1. Then, the procedure advances to Step S212. When the brake portion 34 has already been activated, the operation of the brake portion 34 is continued.

In Step S211 of "DEACTIVATE BRAKE", the brake control unit 43 deactivates the operation of the brake portion 34. Then, the procedure advances to Step S212. When the brake portion 34 has not been activated, a state in which the brake portion 34 is not in operation is continued.

In Step S212 of "CONTROL PERIOD HAS ELAPSED?", the brake control unit 43 determines whether or not one control period has elapsed. When one control period has not elapsed, the brake control unit 43 determines that the current control period has not ended, and continues the processing of Step S210 or Step S211. When one control period has elapsed, the procedure advances to Step S213.

In Step S213 of "MOVE DISTANCE $L_c$?", the brake control unit 43 determines whether or not the continuum robot 1 has been moved by the distance $L_c$ after it is determined in Step S201 that the target angle has been input to the angle input portion 5. When it is determined that the continuum robot 1 has not been moved by the distance $L_c$, the procedure returns to Step S208 to start the subsequent control period. When it is determined that the continuum robot 1 has been moved by the distance $L_c$, the procedure returns to Step S201 illustrated in FIG. 10.

In this manner, when the moving speed of the continuum robot 1 being moved by the user satisfies the condition for preventing the continuum robot 1 from deviating from the target path T, the brake control unit 43 inhibits the brake portion 34 from applying a brake to the drive unit 2. In this case, the user can cause the continuum robot 1 to perform an advancing/reversing action at a desired moving speed (that is, required moving speed). Even when the user causes the continuum robot 1 to perform an advancing/reversing action at a desired speed in this case, the continuum robot 1 does not deviate from the target path T. Meanwhile, when the moving speed of the advancing/reversing action of the continuum robot 1 (drive unit 2) being caused by the user does not satisfy the condition for preventing the continuum robot 1 from deviating from the target path T, the brake control unit 43 controls the brake portion 34 to apply a brake to the drive unit 2. In this manner, the speed of the continuum robot 1 is reduced. Therefore, in this case, the moving speed of the advancing/reversing action of the continuum robot 1 can be maintained at such a speed as to prevent the continuum robot 1 from deviating from the target path T. Then, the control apparatus 4 repeatedly executes this processing at predetermined control periods. According to the above-mentioned configuration, it is possible to prevent the continuum robot 1 from deviating from the target path T when the continuum robot 1 is caused to perform an advancing/reversing action. In addition, the reduction in moving speed of the advancing/reversing action can be suppressed to a minimum. In this manner, the second embodiment can produce the same effects as those of the first embodiment.

Other Embodiments

The above-mentioned embodiments are each described by taking the configuration in which the continuum robot 1 includes the two curvable portions of the first curvable portion 111 and the second curvable portion 112 as an example. However, this disclosure can also be applied to the control of the continuum robot 1 including three or more curvable portions. Assuming that the number of curvable portions is A, when a position $s_A$ of the distal-end curvable portion falls within a range of $nL_c \leq s_A \leq (n+1)L_c$, the position of the i-th curvable portion ($1 \leq i \leq A$) from the proximal end side falls within a range of $(n-A+i)L_c \leq s_A \leq (n-A+i+1)L_c$. Therefore, Mathematical Expression (30) and Mathematical Expression (31) may be used to calculate a target value of an angle of the i-th curvable portion and calculate a followable speed $v_{ui}$ of the i-th curvable portion. Mathematical Expression (30) and Mathematical Expression (31) are expressions obtained by substituting n in Mathematical Expression (18) and Mathematical Expression (28), respectively, by n−A+i.

$$\theta_i = (\psi_{n-A+i+1} - \psi_{n-A+i}) l / L_c + \psi_{n-A+1} \quad \text{Mathematical Expression (30)}$$

$$V_{ui} = L_c / |\psi_{n-A+i+1} - \psi_{n-A+i}| \times r_0 / r_{n-A+i} \times \omega_{max} \quad \text{Mathematical Expression (31)}$$

This disclosure can also be applied to the continuum robot 1 in which the respective curvable portions have mutually different lengths. Further, in each of the embodiments described above, the target angle ψ of the distal-end curvable portion is required to be input each time the continuum robot 1 is advanced by the distance $L_c$, but the distance by which the continuum robot 1 is advanced until the target angle is input may differ from the length of the curvable portion. Assuming that the length between the distal-end curvable portion and the i-th curvable portion is $L_i$, when the position of the distal-end curvable portion is $s_A$, the position of the i-th curvable portion is $s_A - L_i$. In addition, assuming that work of inputting the target angle ψ is performed each time the distal-end curvable portion is advanced by a distance $L_d$, the angle memory portion 42 stores the target angle ψ every integral multiple of $L_d$. At this time, the angle control unit 41 calculates an integer $n_i$ that satisfies $n_i L_d \leq s_A - L_i \leq (n_i+1) L_d$, and reads out the target angles $\psi_{ni+1}$ and $\psi_{ni}$ from the angle memory portion 42. Then, with those target angles being substituted into Mathematical Expression (20) and Mathematical Expression (21), the distal-end angles $\theta_1$ and $\theta_2$ are calculated to perform the speed control of the movement driving unit 32 and the determination regarding the braking to be performed by the brake portion 34.

Further, in each of the above-mentioned embodiments, the angle input portion 5 is described as being configured to be used for inputting the target angle ψ exhibited when the second curvable portion 112 is advanced by the predetermined distance $L_c$, but is not limited to such a configuration. For example, in order to improve operability, in the same manner as in general endoscopes, the angle input portion 5 may be configured to be used for inputting the target angle at the current position. In this case, when the drive unit 2 is advanced in the continuum robot system, the angle control unit 41 uses Mathematical Expression (32), which is obtained by substituting the angle $\psi_{n+1}$ of Mathematical Expression (18) by $\psi_n$, to control the distal-end angle $\theta_2$ of the second curvable portion 112.

$$\theta_2 = \psi_n \quad \text{Mathematical Expression (32)}$$

In accordance with Mathematical Expression (32), the target angle of the second curvable portion 112 is kept constant over the movement distance l ($0 \leq l \leq L_c$) from the current position, and hence it is not required to drive the second angle control motor 212. Therefore, the drive unit speed calculation/control unit 44 controls the movement driving unit 32 through use of only Mathematical Expression (27) relating to the first angle control motor 211. Further, the brake control unit 43 controls the brake portion 34 through use of only Mathematical Expression (27) relating to the first angle control motor 211. Even when the target angle ψ at the current position is input, the target angle input at the time of the advancing action is stored in the angle memory portion 42, and hence at the time of the reversing action, both Mathematical Expression (27) and Mathematical Expression (28) are used to control the movement driving unit 32 and the brake portion 34 in the same manner as in each of the embodiments described above.

Further, in each of the embodiments described above, each time the continuum robot 1 is advanced by the distance $L_c$, the user inputs (sets) the target angle ψ, and the control apparatus 4 acquires the target angle ψ, but is not limited to such a configuration. For example, when the target path T through which the continuum robot 1 is required to pass is known before the advancing action is performed, it is possible to omit the inputting (setting) and the acquisition performed each time the continuum robot 1 is advanced by the distance $L_c$. For example, as a method of calculating the target angle ψ from the target path T, it is possible to employ a method involving first dividing the target path T into a plurality of sections each having a length of $L_c$, calculating the tangential line of the path at an end point of each section, and setting an angle formed between the tangential line at each end point and the $X_1$ axis as the target angle ψ. In this case, it is possible to employ a configuration in which the target path T is stored in advance in the angle memory portion 42 and the drive unit speed calculation/control unit 44 and the brake control unit 43 calculates the target angle ψ through the above-mentioned calculation. It is also possible to employ a configuration in which the user is allowed to store the target angle at each end point of each section of the target path T in an angle memory unit. According to the above-mentioned configuration, it is not required for the user to input the target angle ψ during the advancing/reversing action.

In addition, this disclosure can be applied to a continuum robot configured to three-dimensionally drive one curvable portion through use of a plurality of posture changing units (angle control motors). For example, when the continuum robot system is applied to a flexible endoscope, human organs including an esophagus, a bronchus, a lung, and a large intestine, which are insertion/extraction paths, each have a part curved three-dimensionally. Therefore, in order to insert or extract the continuous body robot 1 along those organs, it is desired to perform a follow-the-leader action while three-dimensionally driving the respective curvable portions through use of the plurality of posture changing units (angle control motors). In this case, the drive unit speed calculation/control unit 44 determines whether or not Mathematical Expression (29) is satisfied for all the posture changing units, and sets the target moving speed based on the determination result. Meanwhile, the brake control unit 43 controls the brake portion 34 so as to have a target angular velocity equal to or lower than the maximum value for all the posture changing units. For example, in the same manner as in the first embodiment, the angular velocity of the motor for satisfying the condition for preventing the curvable portion for deviating from the target path T is calculated from the speed of the drive unit 2. When the required angular velocity exceeds the maximum angular velocity for at least one motor, the brake portion 34 is controlled to apply a brake to the drive unit 2.

In this disclosure, the moving speed of the continuum robot 1 can also be controlled in consideration of a delay in response from the curvable portion that occur due to an upper limit to the acceleration of the motor in addition to the maximum rotation speed of the motor. When Mathematical Expression (31) indicating the condition relating to the maximum speed of the continuum robot 1 is differentiated with respect to time, Mathematical Expression (33) is obtained as follows. The left-hand side of Mathematical Expression (33) represents the acceleration of the continuum robot 1 (drive unit 2), $a_{max}$ on the right-hand side represents the maximum angular acceleration of the motor.

$$\dot{v} \leq L_c / |\psi_{n-A+i+1} - \psi_{n-A-i}| \times r_0 / r_{n-A+i} \times \alpha \quad \text{Mathematical Expression (33)}$$

The drive unit speed calculation/control unit 44 calculates the acceleration of the continuum robot 1 from the moving speed v of the continuum robot 1 acquired from the sensor 24. When the calculated acceleration does not satisfy Mathematical Expression (33), the drive unit speed calculation/control unit 44 sets the target moving speed of the continuum robot 1 to have a value smaller than the value of a maximum speed $v_{max}$. With this configuration, it is possible to perform the follow-the-leader control while driving the motor at an angular acceleration equal to or lower than the maximum angular acceleration. Meanwhile, when the calculated acceleration does not satisfy Mathematical Expression (33), the brake control unit 43 can activate the brake portion 34 to perform the follow-the-leader control while driving the motor at an angular acceleration equal to or lower than the maximum angular acceleration.

Other Application Example

The above-mentioned embodiments are each described by taking an example of applying a continuum robot system to a flexible endoscope, but a target to which a control apparatus for a continuum robot system according to one embodiment of this disclosure is applied is not limited to a flexible endoscope. For example, this disclosure can also be applied to the control of an industrial continuum robot configured to perform work by being inserted into the inside of a pipe or confined space. In this case, the camera provided at the distal end of the continuum robot may be appropriately changed depending on the application target. For example, it is possible to employ a configuration provided with each of different kinds of tools and devices in addition to the camera.

Other Embodiments

This disclosure can also be achieved by processing for supplying a program for implementing at least one of the functions of the above-mentioned embodiments to a system or an apparatus via a network or a storage medium, and reading out and executing the program by at least one processor of a computer included in the system or the apparatus. Further, this disclosure can be achieved by a circuit (for example, ASIC) for implementing at least one of the functions.

In addition, in each of the embodiments described above, the configuration in which the computer including the CPU, the ROM or other such storage medium, and the RAM executes the program to cause the computer to function as the respective components of the control apparatus is described, but this disclosure is not limited to such a configuration. For example, each of the components of the control apparatus may be configured to be separately built in a hardware manner.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

This disclosure relates to a technology suitable for a continuum robot system and a control method for a continuum robot system. According to this disclosure, it is possible to prevent a continuum robot from deviating from a target path when the continuum robot is advanced or reversed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-082323, filed Apr. 18, 2017, which is hereby incorporated by reference herein in its entirety.

What is claimed is:

1. A control apparatus for a continuum robot system, the continuum robot system including:
    a continuum robot, which includes a plurality of curvable portions provided in series in a longitudinal axial direction of the plurality of curvable portions and each being curvable, and is capable of being moved in the longitudinal axial direction;
    a movement driving unit configured to move the continuum robot in the longitudinal axial direction; and
    a posture changing unit configured to cause each of the plurality of curvable portions to curve, to thereby change a posture of the each of the plurality of curvable portions,
the control apparatus comprising:
    a movable drive control unit configured to control the movement driving unit; and
    a speed calculation unit configured to calculate a maximum value of a moving speed of the continuum robot in the longitudinal axial direction, which enables the posture changing unit to cause the posture of each of the plurality of curvable portions to agree with a target posture before the movement driving unit completes moving the continuum robot in the longitudinal axial direction by a predetermined distance,
    wherein the movable drive control unit is configured to set the moving speed of the continuum robot in the longitudinal axial direction, which is being moved by the movement driving unit, to have a value equal to or smaller than the maximum value.

2. The control apparatus for a continuum robot system according to claim 1, wherein the movable drive control unit is configured to calculate the maximum value for each of the plurality of curvable portions, and to set the moving speed to have a value that is smallest among the calculated maximum values.

3. The control apparatus for a continuum robot system according to claim 2, wherein the movable drive control unit is configured to calculate the maximum value for each of the plurality of curvable portions, and to set the moving speed to have a value obtained by multiplying a value that is smallest among the calculated maximum values by a coefficient equal to or smaller than 1.

4. The control apparatus for a continuum robot system according to claim 1, wherein the movable drive control unit is configured to control the moving speed such that the moving speed becomes a speed having a value equal to or larger than a threshold value.

5. The control apparatus for a continuum robot system according to claim 1,
wherein the posture changing unit is provided to one end portion of the plurality of curvable portions in the longitudinal axial direction, and
wherein the posture of each of the plurality of curvable portions is capable of being defined by an angle formed between: a straight line passing a distal part of the each of the plurality of curvable portions and perpendicularly crossing to a center line of the each of the plurality of curvable portions; and a straight line passing a proximal part of a curvable portion that is closest to the posture changing unit among the plurality of curvable portions and perpendicularly crossing to a center line of the proximal part of the curvable portion.

6. A control apparatus for a continuum robot system, the continuum robot system including:
a continuum robot, which includes a plurality of curvable portions provided in series in a longitudinal axial direction of the plurality of curvable portions and each being curvable, and is capable of being moved in the longitudinal axial direction;
a brake portion configured to reduce a moving speed of the continuum robot in the longitudinal axial direction; and
a posture changing unit configured to change a posture of each of the plurality of curvable portions,
the control apparatus comprising:
a speed calculation unit configured to calculate a maximum value of the moving speed of the continuum robot in the longitudinal axial direction, which enables the posture changing unit to cause the posture of each of the plurality of curvable portions to agree with a target posture before the continuum robot completes being moved in the longitudinal axial direction by a predetermined distance; and
a brake control unit configured to control the brake portion,
wherein the brake control unit is configured to cause the brake portion to reduce the moving speed of the continuum robot in the longitudinal axial direction when the moving speed of the continuum robot in the longitudinal axial direction exceeds the maximum value.

7. The control apparatus for a continuum robot system according to claim 6, wherein the brake control unit is configured to calculate the maximum value for each of the plurality of curvable portions, and to cause the brake portion to reduce the moving speed of the continuum robot in the longitudinal axial direction when the moving speed of the continuum robot in the longitudinal axial direction exceeds a moving speed having a value that is smallest among the maximum values.

8. The control apparatus for a continuum robot system according to claim 6,
wherein the posture changing unit is provided to one end portion of the plurality of curvable portions in the longitudinal axial direction, and
wherein the posture of each of the plurality of curvable portions is capable of being defined by an angle formed between: a straight line passing a distal part of the each of the plurality of curvable portions and perpendicularly crossing to a center line of the each of the plurality of curvable portions; and a straight line passing a proximal part of a curvable portion that is closest to the posture changing unit among the plurality of curvable portions and perpendicularly crossing to a center line of the proximal part of the curvable portion.

9. A control apparatus for a continuum robot system, the continuum robot system including:
a continuum robot, which includes a plurality of curvable portions provided in series in a longitudinal axial direction of the plurality of curvable portions and each being curvable, and is capable of being moved in the longitudinal axial direction; and
a posture changing unit configured to change a posture of each of the plurality of curvable portions,
the control apparatus comprising:
a speed calculation unit configured to calculate a maximum value of a moving speed of the continuum robot in the longitudinal axial direction, which enables the posture changing unit to cause the posture of each of the plurality of curvable portions to agree with a target posture before the continuum robot completes being moved in the longitudinal axial direction by a predetermined distance; and
a moving speed limiting unit configured to limit the moving speed of the continuum robot in the longitudinal axial direction to a speed having a value equal to or smaller than the maximum value.

10. The control apparatus for a continuum robot system according to claim 9,
wherein the posture changing unit is provided to one end portion of the plurality of curvable portions in the longitudinal axial direction, and
wherein the posture of each of the plurality of curvable portions is capable of being defined by an angle formed between: a straight line passing a distal part of the each of the plurality of curvable portions and perpendicularly crossing to a center line of the each of the plurality of curvable portions; and a straight line passing a proximal part of a curvable portion that is closest to the posture changing unit among the plurality of curvable portions and perpendicularly crossing to a center line of the proximal part of the curvable portion.

* * * * *